United States Patent [19]

Sachs et al.

[11] Patent Number: 5,436,243
[45] Date of Patent: Jul. 25, 1995

[54] AMINOANTHRAQUINONE DERIVATIVES TO COMBAT MULTIDRUG RESISTANCE

[75] Inventors: Clifford W. Sachs; Robert L. Fine, both of Durham; Lawrence M Ballas, Apex; R. Ivy Carroll; Robert Bell, both of Durham, all of N.C.

[73] Assignees: Research Triangle Institute Duke University, Research Triangle Park, N.C.; Pharmaceuticals Corporation, Durham, N.C.

[21] Appl. No.: 152,894

[22] Filed: Nov. 17, 1993

[51] Int. Cl.⁶ .................. A61K 31/135; A61K 31/55; A61K 31/535; A61K 31/445

[52] U.S. Cl. .................. 514/231.8; 514/237.5; 514/239.5; 514/252; 514/255; 514/316; 514/319; 514/325; 514/649; 544/79; 544/156; 544/357; 544/380; 546/191; 546/204; 552/247; 552/255

[58] Field of Search .................. 544/79, 156, 357, 380; 546/191, 204; 552/247, 255; 514/231.8, 237.5, 239.5, 252, 255, 316, 319, 325, 649

[56] References Cited

U.S. PATENT DOCUMENTS

| | | | |
|---|---|---|---|
| 3,960,751 | 6/1976 | Moriyama et al. | 252/299 |
| 4,197,249 | 4/1980 | Murdock et al. | 260/380 |
| 4,310,666 | 1/1982 | Zee-Cheng et l. | . |
| 4,526,989 | 7/1985 | Murdock et al. | 549/316 |
| 4,540,788 | 9/1985 | Murdock | 546/284 |
| 4,598,155 | 7/1986 | Adam | 548/253 |
| 4,675,283 | 6/1987 | Roninson | 435/6 |
| 4,732,893 | 3/1988 | Pasini et al. | 552/247 X |
| 4,762,648 | 9/1988 | Stache et al. | 260/383 |
| 4,765,972 | 8/1988 | Safa et al. | 424/1.1 |
| 4,782,056 | 11/1988 | Rösner et al. | 514/242 |
| 4,816,450 | 3/1989 | Bell et al. | 514/25 |
| 4,837,306 | 6/1989 | Ling et al. | 530/387 |
| 4,894,451 | 1/1990 | Krapcho et al. | 544/156 |
| 4,897,403 | 1/1990 | Martin et al. | 514/313 |
| 4,904,582 | 2/1990 | Tullis | 435/6 |
| 4,911,924 | 3/1990 | Griffith et al. | 424/114 |
| 4,923,871 | 5/1990 | Inaba et al. | 514/255 |
| 4,973,675 | 11/1990 | Israel et al. | 536/6.4 |
| 4,990,538 | 2/1991 | Harris et al. | 514/648 |
| 4,996,321 | 2/1991 | Baldwin et al. | 546/194 |
| 4,999,344 | 3/1991 | Jett-Tilton et al. | 514/77 |
| 5,004,758 | 4/1991 | Boehm et al. | 514/283 |
| 5,005,588 | 4/1991 | Rubin | 128/804 |
| 5,021,426 | 6/1991 | Baldwin et al. | 514/313 |
| 5,025,020 | 6/1991 | Van Dyke | 514/280 |
| 5,055,459 | 10/1991 | Andersson et al. | 514/114 |
| 5,091,552 | 2/1992 | Farquhar | 558/180 |
| 5,104,858 | 4/1992 | Hait et al. | 514/34 |
| 5,112,817 | 5/1992 | Fukazawa et al. | 514/183 |
| 5,114,919 | 5/1992 | Baldwin et al. | 514/11 |
| 5,114,951 | 5/1992 | King | 514/290 |
| 5,124,330 | 6/1992 | King | 514/250 |
| 5,124,338 | 6/1992 | King | 514/343 |
| 5,124,339 | 6/1992 | King | 514/352 |
| 5,130,303 | 7/1992 | Akiyama et al. | 514/85 |
| 5,134,168 | 7/1992 | Bitonti et al. | 514/655 |
| 5,160,727 | 11/1992 | Klohs et al. | 424/10 |
| 5,173,486 | 12/1992 | Monkovic et al. | 514/211 |
| 5,182,267 | 1/1993 | Ogawa et al. | 514/34 |
| 5,182,293 | 1/1993 | Sunkara et al. | 514/340 |
| 5,182,387 | 1/1993 | Freedman et al. | 540/590 |
| 5,187,266 | 2/1993 | Farquhar et al. | 536/6.4 |
| 5,190,957 | 3/1993 | Sunkara et al. | 514/314 |

FOREIGN PATENT DOCUMENTS 639298 4/1964 Belgium .
1794385 5/1974 Germany .

(List continued on next page.)

OTHER PUBLICATIONS

Ogasawara et al., "Potentiation of Vincristine Cytotoxicity by Ruginone B1 and Piperasfizine A in Human Moser and K562 Cells–Mode of Action", *J. Antibiotics,* 45(1):129–132(1992).

(List continued on next page.)

*Primary Examiner*—Richard L. Raymond
*Attorney, Agent, or Firm*—Banner & Allegretti, Ltd.

[57] ABSTRACT

Potentiating agents inhibit the development of multi-drug resistance, reduce drug-resistance in drug-resistant tumors, or sensitize tumors to antineoplastic drugs, thereby potentiating the effect of antineoplastic agents. The potentiating agents are aminoanthraquinones, preferably 1,4-bis(N-substituted) amino anthraquinones, and pharmaceutically acceptable salts thereof.

20 Claims, 13 Drawing Sheets

FOREIGN PATENT DOCUMENTS

| | | |
|---|---|---|
| 2835661A1 | 3/1979 | Germany . |
| 2000029A | 1/1979 | United Kingdom . |
| PCT/US90/-04440 | 8/1989 | WIPO . |
| PCT/US89/-04394 | 10/1989 | WIPO . |
| PCT/GB90/-00935 | 6/1990 | WIPO . |
| PCT/US90/-06141 | 10/1990 | WIPO . |
| WO 92/07557 | 10/1991 | WIPO . |
| WO 92/07558 | 10/1991 | WIPO . |
| PCT/US91/-08026 | 10/1991 | WIPO . |
| PCT/GB91/-02248 | 12/1991 | WIPO . |
| PCT/EP92/-00408 | 2/1992 | WIPO . |
| PCT/US92/-00974 | 2/1992 | WIPO . |
| PCT/US92/-03085 | 4/1992 | WIPO . |
| PCT/US92/-03999 | 5/1992 | WIPO . |

OTHER PUBLICATIONS

Sachs, et al., "Protein Kinase C Inhibitors Increase Drug Accumulation and Decrease Resistance of Multidrug Resistant Cell Lines", *Proc. Amer. Assoc. Cancer Res.*, 32:373, Abstract 2218, 1991.

Fine, "Multidrug Resistance", Pinedo, et al., (eds) *Cancer Chemotherapy and Biological Response Modifiers*, pp. 73–84, NY; Elsevier Scientific Publishers, 1988.

Ford, et al., "Pharmacology of Drugs that Alter Multidrug Resistance in Cancer", *Pharmacological Reviews* 42(3);155–199(1990).

Bellamy, et al., "The Clinical Relevance of Multidrug Resistance", *Cancer Investigation*, 8(5):547–562(1990).

Ford, et al., "Cellular and Bilchemical Characterization of Thioxanthenes for Reversal of Multidrug Resistance in Human and Murine Cell Lines", *Cancer Res.*, 50:1748–1756(1990).

Ford, et al., "Structural Features Determining Activity of Phenothiazines and Related Drugs for Inhibition of Cell Growth and Reversal of Multidrug Resistance", *Molecular Pharmacology*, 35:105–115(1988).

Pearce, et al., "Essential Features of the P-glycoprotein Pharmacophore as Defined by a Series of Reserpine Analogs that Modulate Multidrug Resistance", *Proc. Natl. Acad. Sci. USA*, 86:5128–5132(1989).

Zamora, et al., "Physical-Chemical Properties Shared by Compounds that Modulate Multidrug Resistance in Human Leukemic Cells", *Molecular Pharmacology*, 33:454–462(1988).

Cornwall, et al., "Increased Vinblastine Binding to Membrane Vesicles from Multidrug-Resistant KB Cells", *J. Biol. Chem.* 261(17):7921–7928(1986).

Cornwell, et al., "Certain Calcium Channel Blockers Bind Specifically to Multidrug-Resistant Human KB Carcinoma Membrane Vesicles and Inhibit Drug Binding to P-glycoprotein", *J. Biol. Chem.*, 262(5):2166–2170(1987).

Cornwell, et al., "Membrane Vesicles from Multidrug-Resistant Human Cancer Cells Contain a Specific 150-to 170-kDa Protein Detected by Photoaffinity Labeling", *Proc. Natl. Acad. Sci. USA*, 83:3847–3850(1986).

Naito, et al., "ATP/$Mg^{2+}$-Dependent Binding of Vincristine to the Plasma Membrane of Multidrug-Resistant K562 Cells", *J. Biol. Chem.*, 263(24):11887–11891(1988).

Safa, et al., "Identification of the Multidrug Resistance-Related Membrane Glycoprotein as an Acceptor for Calcium Channel Blockers", *J. Biol. Chem.*, 262(16):7864–7888(1987).

Tamai, et al., "Competitive Interaction of Cyclosporins with the *Vinca* Alkaloid-Binding Site of P-glycoprotein in Multidrug-Resistant Cells", *J. Biol. Chem.*, 265(27):16509–16513(1990).

Center, et al., "Mechanisims Regulating Cell Resistance to Adrimycin", *Ciochem. Pharma.* 34(9):1471–1476(1985).

Hamada, et al., "Phosphorylation of the M,170,000 to 180,000 Glycoprotein Specific to Multidrug-Resistant Tumor Cells: Effects of Verapamil, Thrfluoperazine, and Phorbot Esters", *Cancer Research* 47:2869–2865(1987).

Meyers, "Protein Phosphorylation of Multidrug-Resistant Chinese Hamster Cells", *Cancer Communications*, 4(4):23≧241(1989).

Blobe, et al., "Selective Regulation of Expression of Protein Kinase C (PKC) Isoenzymes in Multidrug-Re-

OTHER PUBLICATIONS sistant MCF-7 Cells", *J. Biol. Chem.,* 268(1):658-664(1993).

Chambers, et al., "Protein Kinase C Phosphorylates P-glycoprotein in Multidrug Resistant Human KB Carcinoma Cells", *J. Biol. Chem.,* 265(13):7679-7686(1990).

Fine, et al., "Phorbol Esters Induce Multidrug Resistance in Human Breast Cancer Cells", *Proc. Natl. Acad. Sci. USA,* 85:582-586(1988).

Fojo, et al., "Expression of a Multidrug-Resistance Gene in Human Tumors and Tissues", *Proc. Natl. Acad. Sci. USA,* 84:265-269(1987).

Dalton, et al., "Drug-Resistance in Multiple Myeloma and Non-Hodgkins'a Lymphoma: Detection of P-Glycoprotein and Potential Circumvention by Addition of Verspamil toChemotherapy", *J. Clin. Oncology,* 7(4):415-424(1989).

Ozols, et al., "Verapamil and Adriamycin in the treatment of Drug-Resistant Ovarian Cancer Patients", *J. Clin. Oncology,* 5(4)641-647(1987).

Murdock et al., "Antitumor Agents. 1.1,4-Bis[(aminoalky)amino]-9,10-anthracenediones", *J. Medicinal Chemistry,* 22(9):10214-1030(1979).

ZEE-Cheng et al., "Antineoplastic Agents. Structure-Activity Relationship Study of Bis(substituted aminoalkylamino) Anthraquinones", *J. Medicinal Chemsitry,* 21(3):291-294(1978).

International Search Report dated Mar. 17, 1995 for International Application No. PCT/US94/13235.

Sachs, et al., "Protein Kinase C (PKC) Inhibitors Increase Drug Accumulation and are Cytotoxic to a Human Multidrug Resistant (MDR) Breast Cancer Line", *Proc. Amer. Assoc. for Cancer Res.,* 31:359, Abstract 2128, 1990.

Ballas, et al., "Mitoxantrone Inhibits Serine/Threonine Kineases Associated with Signal Transduction and Milogenesis", *Proc. Amer. Assoc. Cancer Res.,* 32:394, Abstract 2344, 1991.

AMINOANTHRAQUINONE DERIVATIVES TO COMBAT MULTIDRUG RESISTANCE

This invention was made with government support under Grant No. 5U01-CA-46738 awarded by the National Cancer Institute. Research laboratories supported by the Durham Veterans Administration Medical Center were used in the performance of this research. The government has certain rights in this invention.

FIELD OF THE INVENTION

The present invention relates to the use of N-substituted alkyl amino anthraquinones and salts thereof as chemotherapeutic agents for neoplasms resistant to multiple drugs. The present invention more particularly relates to the use of such compounds as agents for enhancing the therapeutic effect of other antitumor agents.

BACKGROUND OF THE INVENTION

Complete cures of various tumors like leukemias, lymphomas and solid tumors by the use of chemotherapeutic agents are not frequently achieved because of heterogeneous sensitivity of tumor cells to each antitumor agent. Cancer chemotherapy also fails because of intrinsic resistance of the tumor to various drug therapies. In other cases, a tumor may become resistant to the antitumor agents used in a previous treatment. The therapeutic effects of these agents are then lost. An even graver problem is that recurrent and relapsed cancers are resistant not only to the anticancer drugs used in previous treatments, but also manifest resistance to other antitumor agents, unrelated to the drug used previously either by chemical structure or by mechanism of action. These phenomena are collectively referred to as multidrug resistance.

The emergence of drug resistance represents a major obstacle to the successful treatment of cancers which can be treated by chemotherapy. To circumvent the problem of clinical drug resistance, chemotherapy may utilize combinations or successive treatments with functionally and structurally diverse antineoplastic agents to minimize the development of drug resistance and maximize the response to therapy. Despite this approach, most cancer patients relapse or never respond because of the development of drug resistance and further responses to therapy are limited (Chabner et. al., *Cancer* 54:2599–2608 (1984)).

The origins of tumor cell drug resistance in cancers which initially respond to chemotherapy are not fully understood. According to one theory, the somatic mutation theory, tumor cells are characterized by genetic instability (Goldie et al., *Cancer Res.* 44:3643–3653 (1984)), with observed frequencies of mutation to drug resistance of one in $10^5$ to $10^7$ (Bellamy et at., *Cancer Invest.* 8:547–562 (1990)). Since a detectable tumor mass of 1 cm$^2$ (approximately 1 g) contains at least $10^9$ cells, it is nearly certain that some of the cells are resistant at the time of diagnosis prior to chemotherapy (Id.).

Cancer cells may become refractory to chemotherapy by several mechanisms. One type of drug resistance, called multidrug resistance, arises in cancer cells exposed to anticancer drugs derived from natural products (i.e., antineoplastic agents isolated from plants, fungi or bacteria). It can develop in cancer cells exposed to a single natural antineoplastic drug. In multidrug resistant (MDR) cells, cross resistance is observed to natural product antineoplastic agents (Vinca alkaloids, anthracyclines, epipodophyllotoxins, colchicine, actinomycin D and antibiotics) (See I. Pastan and M. Gottesman, *New England J. Med.* 1388, 1389 Table 1 (May 28, 1987)), but not alkylating anticancer drugs, bleomycin, or antimetabolites. The MDR phenotype is characterized by: (1) decreased intracellular accumulation of natural product anticancer drugs, secondary to their enhanced efflux; (2) cross resistance to other structurally and functionally unrelated natural product antineoplastic drugs; and (3) overexpression of a high molecular weight (150–170 kilodalton) transmembrane protein, termed the P-glycoprotein (the multiple drug transporter) which acts as drug transport pump. P-glycoprotein is an ATPase which functions by pumping structurally diverse antitumor drugs from cells. (See R. Fine and B. Chabner, *Multidrug Resistance, in Cancer Chemotherapy*, 117–128 (H. Pinedo and B. Chabner eds. 1986)(reviewed in Fine et al., Multidrug Resistance, Cancer Chemotherapy and Biological Response Modifiers, Eds: Pinedo, HM, Longo, DL and Chabner, BA. Elsvier Scientific Publications, NY, NY (1988)); Moscow et al., *J. National Cancer Institute*, vol. 80, 14–20 (1988); and Ford et al., *Pharmacol. Rev.* 42:155–199 (1990)).

A number of studies have implicated the P-glycoprotein in the MDR phenotype. The presence of the P-glycoprotein generally correlates with resistance in MDR cell lines (Kartner et al., *Science* 221:1285–1288 (1983)). The degree of resistance of certain tumor cells has been documented to correlate with both elevated expression of the drug transporter and reduced accumulation of antitumor drugs. (See A. Fojo et al., *Cancer Res.* 45:3002–3007 (1985).) Tumor cells expressing elevated levels of the multiple drug transporter accumulate far less antitumor agents intracellularly than tumor cells having low levels of the P-glycoprotein. Further, drug sensitive cells stably transfected with the mdr1 gene overexpress the P-glycoprotein and exhibit the MDR phenotype (Schurr et al., *Cancer Res* 49:2729–2734 (1989); Hammond et al., *Cancer Res.* 49:3867–3871 (1989); Sugimoto et al., *Cancer Res.* 47:2720–2726 (1987)). The role of P-glycoprotein as an energy dependent efflux pump is supported by the findings that depletion of cellular ATP in MDR cells eliminates the reduced drug accumulation defect of MDR cells (Dano, *Biochimica et Biophysica Acta* 323:466–483 (1973)), that the purified P-glycoprotein has ATPase activity (Hamada et al., *J. Biol. Chem.* 263:1454–1458 (1988)), and that expression of human DNA coding for P-glycoprotein confers high activity drug stimulatable ATPase activity (Sarkadi, B. et al., *J. Biol. Chem.* 267:4854–4858, 1992). Using antibodies to the P-glycoprotein, membrane vesicles prepared from MDR cell lines have been shown to contain this protein which is absent from membrane vesicles of parental drug sensitive cell lines by Western blot methods. The P-glycoprotein found in membrane vesicles of MDR cells shows specific binding of radiolabeled anticancer drugs and photoactive drug analogs. Membrane vesicles prepared from drug sensitive cell lines do not show specific binding of these compounds (Cornwell et al., *J. Biol. Chem.* 261:7921–7928 (1986); Cornwell et al., *Proc. Natl. Acad. Sci., USA* 83:3847–3850 (1986); Naito et al., *J. Biol. Chem.* 263:1187–11891 (1989)). Nucleotide sequence analysis of the mdr1 gene indicates that it codes for a 1280 amino acid protein with 12 transmembrane regions and 2 nucleotide binding sites. The deduced amino acid sequence of the P-glycoprotein shows extensive homology with the bacterial membrane transport protein for hemolysin B (Gerlach et al., *Nature* 324:485–489 (1986); Gros et al., *Cell* 47:371–380 (1986); Chen et al., *Cell* 47:381–389 (1986)).

A role for the P-glycoprotein in clinical drug resistance is suggested by several studies which have utilized specific monoclonal antibodies to the P-glycoprotein or cDNA probes to measure mdr1 RNA levels in tumors. High levels of the P-glycoprotein have been detected in drug-refractory hematologic malignancies, ovarian cancers, neuroblastomas, and sarcomas. These cancers usually respond initially to chemotherapy, but become refractory to further treatment and are considered to have acquired resistance. Other tumors documented to initially be drug-sensitive but to then become drug resistant include pheochromocytoma, acute lymphocytic leukemia in adults, acute nonlymphocytic leukemia in adults, nodular poorly differentiated lymphoma and breast cancer. High levels of the P-glycoprotein have also been found in untreated colon, renal, adrenal, and hepatic carcinomas which do not respond well to chemotherapy (reviewed in Bellamy et al., *Cancer Invest.* 8:547–562 (1990)). Interestingly, P-glycoprotein RNA expression is high in normal kidney, adrenal, hepatic and colonic tissues (Fojo et al., *Proc. Natl. Acad. Sci., USA*, 84:265–269 (1987)). These tissues have major roles in detoxification and secretion of toxins, suggesting a possible protective physiological role for the P-glycoprotein in normal tissues. Adult tumors derived from these tissues usually do not respond to chemotherapy. These types of tumors are considered to have intrinsic resistance. Other tumors documented to express high levels of the multidrug transporter include pancreatic, carcinoid, and chronic myelogenous leukemia in blast crisis. Increased levels of mdr1 expression have been found in untreated tumors derived from the colon, liver, kidney, adrenal gland, and pancreas which are considered to be intrinsically resistant (Goldstein et al., *J. Natl. Cancer Inst.* 81:116–124 (1989)).

It is likely that several mechanisms other than reduced drug accumulation may play a role in drug resistance. These include differences in DNA repair capacities, increased detoxification of anticancer drugs, alterations of the drug targets, and alterations of subcellular distributions of anticancer drugs which decrease drug concentrations at their targets (Fine, "Multidrug Resistance, Cancer Chemotherapy and Biological Response Modifiers", Eds: Pinedo, HM, Longo, DL and Chabner, BA. Elsvier Scientific Publications, NY, NY (1988); Moscow et al., *J. National Cancer Institute*, vol. 80, 14–20 (1988); Ford et al., *Pharmacol. Rev.* 42:155–199 (1990); Endicott et al., *Annual Rev. Biochem.* 58:137–171 (1989)). However, the P-glycoprotein is considered to be the major determinant of the MDR phenotype.

There is substantial evidence to suggest that P-glycoprotein function can be modulated by phosphorylation of the P-glycoprotein by cellular kinases, notably protein kinase C (PKC). Many MDR phenotype inhibitors are also PKC inhibitors. A number of laboratories have reported increased PKC activity in MDR cell lines and an association between PKC stimulation and the MDR phenotype (Palayoor et al. Biochem & Biophys. Res. Comm. 148:718–721 (1987); Fine et al., *Proc. Natl. Acad. Sci., USA* 85:582–587 (1988); Posada et al., *Cancer Res.* 49:6634–6640 (1989); Ferguson et al., *Cancer Res.* 47:433–441 (1987); O'Connor et al., Leuk. Res. 9:885–895 (1985); O'Brian et al., *FEBS Lett.* 246: 78–82 (1989); and Posada et al., Cancer Commun. 1:285–292 (1989)). In the MCF7 cell line, activation of PKC by phorbol ester has been shown to reduce intracellular accumulation of vincristine and doxorubicin, to transiently induce the MDR phenotype in sensitive, wild type (MCF7 wt) cells and to increase the MDR phenotype in the MDR MCF7 (MCF7 Adr 10) cells (Fine et al., *Proc. Natl. Acad. Sci., USA* 85:582–587 (1988)). The P-glycoprotein has been shown to be phosphorylated by a number of cellular kinases, including PKC (Yu et al., *Cancer Commun.* 3:181–189 (1991); and Chambers et al., *J. Biol. Chem.* 265:7679–7686 (1990)). Interestingly, phorbol esters, and verapamil, a calcium channel blocker, inducers and an inhibitor of the MDR phenotype, respectively, increased phosphorylation of the P-glycoprotein on different serine residues of the protein (Hamada et at., *Cancer Res.* 47:2860–2865 (1987); and Chambers et al., *J. Biol. Chem.* 265:7679–7686, 1990). Also interestingly, a cell line that was transfected with copies of the mdr1 gene did not express an MDR phenotype equivalent to adriamycin selected cells, yet expressed equivalent amounts of P-glycoprotein. When these cells were transfected with the α isoenzyme of PKC, their level of the MDR phenotype increased substantially, and was associated with P-glycoprotein phosphorylation and decreased drug accumulation (Yu et at., *Cancer Commun.* 3:181–189 (1991)). Reversal of the MDR phenotype probably involves multiple mechanisms, including inhibition of anticancer drug binding to P-glycoprotein, inhibition of P-glycoprotein efflux, and changes in P-glycoprotein phosphorylation.

There are two major strategies to overcome the problem of the MDR phenotype. One approach is to create new antineoplastic drugs or develop analogues of antineoplastic drugs currently used which are cytotoxic to MDR cancer cells. Two examples of anticancer drugs to which some MDR cells show less cross-resistance are mitoxantrone (Novantrone; see U.S. Pat. No. 4,197,249), a new antineoplastic agent, and morpholino anthracycline analogues of adriamycin and daunomycin. (Coley et at., *Cancer Chemother. Pharmacol.* 24:284–290 (1989)). The second approach to overcome the problem of the MDR phenotype is to identify resistance modifiers which reduce the degree of resistance in MDR cell lines in vitro. Such modifiers would be agents that inhibit the active efflux of antitumor agents by the drug transporter and/or agents that potentiate the efficacy of chemotherapeutic agents. The pharmacology and biochemistry of these types of resistance modifiers are extensively reviewed in Ford et at., *Pharmacol. Rev.* 42:155–199 (1990) and briefly summarized below for the most promising major resistance modifiers. These compounds are being or have been tested in clinical trials. They include calcium channel blockers, calmodulin antagonists, cyclosporins, and hormonal analogs.

Verapamil, a calcium channel blocker, was the first described resistance modifier and is probably the most potent in vitro resistance modifier previously known. Numerous investigators have described increases in accumulation and decreases in resistance to natural product chemotherapeutic drugs in a number of different MDR cells treated with verapamil and other calcium channel blockers. The mechanism by which verapamil, other calcium channel blockers, and calmodulin antagonists are thought to increase drug accumulation is by competing with anticancer drugs for binding to the P-glycoprotein, thereby inhibiting efflux of drug (Cornwell et al., *J. Biol. Chem.* 261:7921–7928 (1986); Cornwell et at., *J. Biol. Chem.* 262:2166–2170 (1986); Safa et at., *J. Biol. Chem.* 7884–7888 (1987); and Akiyama et at., *Mol. Pharmacol.* 33:144–147 (1988)).

Verapamil has been tested in Phase I and Phase II clinical trials (Benson et al., *Cancer Treat Rep.* 69:795–799 (1985); Preasant et al., *Am. J. Clin. Oncol.* 9:355–357 (1986); and Ozols et at., *J. Clin. Oncol.* 5:641–647 (1987)). However, the major problem associated with using verapamil to reverse drug resistance in patients is that it has dose-limiting cardiac toxicity due to blocking of the atrioventricular node. This toxicity prevents its use at concentrations required to reverse drug resistance in vitro. Thus, the lack of response observed in those studies may stem from the inability to achieve high enough concentrations to modulate clinical drug resistance. In a recent study, 3 of 6 patients with clinically resistant, P-glycoprotein positive myeloma responded to a regimen consisting of continuous infusion vincristine, adriamycin (i.e., doxorubicin) plus oral dexamethasone (VAD regimen) when verapamil was included in the regimen by continuous I.V. infusion. These patients had progressive disease while on the VAD regimen prior to the addition of verapamil (Dalton et at., *J. Clin. Oncol.* 7:415–424 (1989)).

Most studies of verapamil's effects on multidrug resistance have utilized racemic mixtures of the drug. The L form of verapamil is 10 times more active as a calcium antagonist than the D form of this compound, although both forms of verapamil increase drug accumulation to a similar extent (Gruber et al., Int. J. Cancer 41:224–229 (1988); and Mickish et at., Cancer Res. 50:3670–3674 (1990)). The use of the D form of this compound is an approach which may circumvent the obstacle of cardiovascular toxicity of calcium channel blockers, such as verapamil. However, more recent studies suggest that even D-verapamil is too toxic to use at high concentrations in humans.

A number of calmodulin antagonists have been found to be good resistance modifiers in vitro. Trifluoperazine, a phenothiazine antipsychotic drug, has been noted to increase drug accumulation and decrease resistance in MDR cell lines (Tsuruo et al., *Cancer Res.* 43:2905–2910 (1983); and Ford et al., *Mol. Pharmacol* 35:105–115 (1989)). Although the increases in drug accumulation were comparable to verapamil in these studies, verapamil was more effective in reversal of resistance to anticancer drugs in other studies (Tsuruo et at., *Cancer Res.* 43:2905–2910 (1983); and Ford et al., *Mol. Pharmacol.* 35:105–115 (1989)). In a clinical trial that combined oral trifluoperazine with constant infusion of adriamycin, 36 patients with tumors clinically resistant to adriamycin were treated. One complete response and six partial responses were noted. Neurotoxicity of trifluoperazine to the extrapyramidal tracts was dose-limiting. The plasma concentrations of trifluoperazine were approximately 10-fold less than the concentrations found to be optimal for modulation of chemoresistance in vitro (Miller et at., J. Clin. Oncol. 6:880–888 (1990)).

The thioxanthene class of antipsychotic drugs are similar in structure to the phenothiazines. The similarity is apparent when comparing the structures of thioxanthene and phenothiazine:

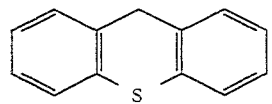

Thioxanthene

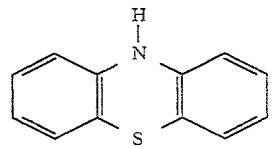

Phenothiazine

A number of these compounds have recently been evaluated for the ability to reverse the MDR phenotype in MDR cell lines (Miller et at., *J. Clin. Oncol.* 6: 880–888, 1990.). Trans-flupenthixol, a thioxanthene, increased doxorubicin accumulation and reversed the MDR phenotype more effectively in a number of MDR cell lines than verapamil (Ford et at., *Cancer Res.* 50:1748–1756 (1990)). The trans isomer of flupenthixol was a much less potent antipsychotic in clinical trials than the cis isomer of this compound (Ford et at., Cancer Res 50:1748–1756 (1990)). It may be a more promising resistance modifier than trifluoperazine if it has less neurotoxicity.

The cyclosporins are immunosuppressive agents which can also potentiate toxicity of anticancer agents at clinically achievable concentrations. In some cell lines, it appears to enhance toxicity and increase drug accumulation in sensitive and resistant cells (Chambers et al., *Cancer Res.* 49:6275–6279 (1989)). Cyclosporin A (CsA) competitively inhibits vincristine and vinblastine binding to the P-glycoprotein (Tamai et at., *J. Biol. Chem.* 265:16509–16513 (1990)). Both Cylcosporin A and its nonimmunosuppressive analog, O-acetyl C9-cyclosporin A (SDZ 33–243) inhibit [$^3$H] azidopine photoaffinity labeling of P-glycoprotein in intact MDR cells and in MDR membrane vesicles (Tamai et at.. *J. Biol. Chem.* 266:16796–16800 (1991)). The use of cyclosporin A to modulate drug resistance may be hampered by irreversible nephrotoxicity and immunosuppression in patients already compromised by myelosuppressive chemotherapy, whereas the use of nonimmunosuppresive cyclosporin analogs may be less toxic.

Hormonal analogs such as the antiestrogens tamoxifen and toremifene are employed in the chemotherapy of breast cancers. These compounds can also modulate resistance of estrogen receptor-negative MDR cell lines via estrogen receptor independent mechanisms (Ramu et at., *Cancer Res.* 44:4392–4395 (1984); and Bermin et al., *Blood* 77:818–825 (1991)). Tamoxifen and tamoxifen metabolites have been found to increase drug accumulation and decrease vinblastine resistance in intrinsically resistant renal cell carcinoma cell lines (Fine et al., Proceedings of the AACR Annual Meeting Abstract #2125 (1990)). The concentrations which elicited these responses were comparable to plasma concentrations achieved in patients participating in Phase I clinical trials to tamoxifen conducted at Duke University, which concentrations were associated with minimal neurologic toxicity that was reversible with cessation of tamoxifen and partial responses to the vinblastine-tamoxifen regimen (Trump, E. L. *J. Natl. Cancer Inst.* 84: 1811–1816, 1992).

In summary, a number of studies have demonstrated that multidrug resistance mediated by the function of the P-glycoprotein occurs in both cultured cell lines and human cancers. The identification of several pharmacologic agents which can antagonize the MDR phenotype in the laboratory has not, to date, identified resistance modifiers with good clinical efficacy, primarily due to doselimiting toxicity of the resistance modifiers. Thus there is a need in the art for means to overcome multidrug resistance expressed by tumors and for means to potentiate the effects of chemotherapeutic agents, in general.

SUMMARY OF THE INVENTION

An object of the present invention is to provide pharmaceutical formulations for enhancing the therapeutic effect of antineoplastic agents by administering to a subject harboring a tumor a compound of Formula (I) or Formula (II) or a pharmaceutically acceptable salt thereof or combinations thereof (hereafter referred to as the "potentiating agent"):

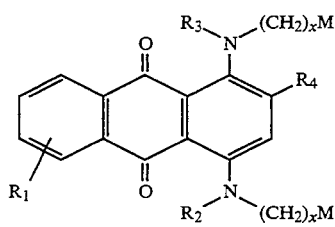

Formula I and

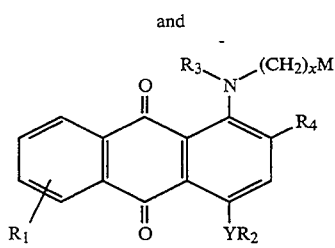

Formula II wherein:
$R_1$ is H or an alkyl chain with 1–7 carbon atoms;
$R_2$ is H or an alkyl chain with 1–7 carbon atoms;
$R_3$ is H or an alkyl chain with 1–7 carbon atoms;
$R_4$ is H or an alkyl chain with 1–7 carbon atoms;
x is an integer ranging from 3 to 12;
Y is O or NH; and
M is selected from the following groups:

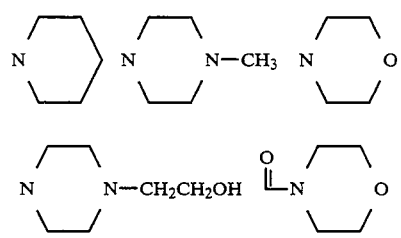

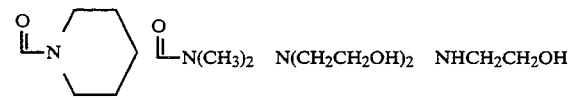

Preferably the potentiating agents are those wherein M is selected from the following groups:

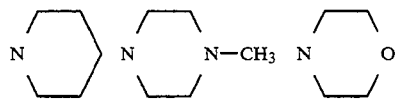

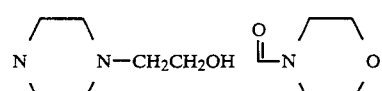

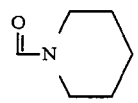

More preferably, the potentiating agents are compounds according to Formula I or a pharmaceutically acceptable salt thereof or combinations thereof wherein $R_1$, $R_2$, $R_3$, and $R_4$ are H.

The pharmaceutical formulation containing a potentiating agent may optionally contain an antineoplastic agent in a pharmaceutically acceptable carder.

Another aspect of the present invention is a method of increasing the sensitivity of tumor cells to an antineoplastic agent to which the tumor cells are resistant, by administering to the resistant tumor cells a potentiating agent concurrently or sequentially with an antineoplastic agent. Resistance to the antineoplastic agent may (a) be an intrinsic property of the tumor cells or (b) develop in response to prior treatment with said antineoplastic agent or another antineoplastic agent capable of selecting for the MDR phenotype.

According to another aspect of the invention a method is provided for selectively inhibiting the growth of tumor cells in a subject in need of such treatment. An antineoplastic agent and a potentiating agent are concurrently or sequentially administered to the subject. The potentiating agent is administered in an amount effective to (a) reduce the amount of the antineoplastic agent required to achieve a growth inhibiting effect on the tumor cells relative to the amount required to achieve the same effect by antineoplastic agent without administration of the potentiating agent; or (b) inhibit the development of the multidrug resistance phenotype in tumor cells.

Yet another aspect of the invention is the use of compounds of Formula I for the sensitization of tumor cells to Vinca alkaloids.

Another aspect of the present invention is the use of a potentiating agent as disclosed herein for the manufacture of a medicament for the inhibition of the multidrug resistance in tumors.

As part of the present invention, alkyl aminoanthraquinones have been indentified as inhibitors of the MDR phenotype in a human breast cancer cell line, MCF7 Adr 10. One such potent compound is 1,4-bis-[3'-(N-morphilino)propyl amino]anthraquinone:

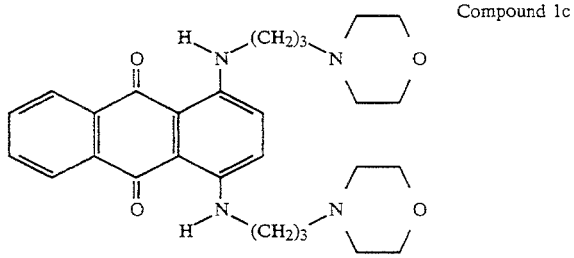

Compound 1c

In contrast to most of the previously described multi-drug resistance inhibitors which have activity at micromolar concentrations, Compound 1c has been found to inhibit Vinca alkaloid drug resistance at nanomolar concentrations. Compound 1c also inhibits resistance to the anthracycline antineoplastic drugs, adriamycin and daunorubicin, in MDR cells and enhances toxicity of vincristine in the parental, drug sensitive, breast cancer cell line, MCF7 WT. Compound 1c has been shown to modulate the drug accumulation defect of a MDR human breast cancer cell line and intrinsically resistant, human, renal cell carcinoma cell lines. In all of these systems, its activity has been found to be comparable or superior to that of verapamil, a previously described, resistance modifier. Compound 1c has a large therapeutic index for bone marrow cytotoxicity versus cancer cell cytotoxicity. Preliminary animal studies show that compound 1c is not toxic at 400 mg/kg in mice.

IN THE DRAWINGS

DETAILED DESCRIPTION OF THE INVENTION

Figure 1:
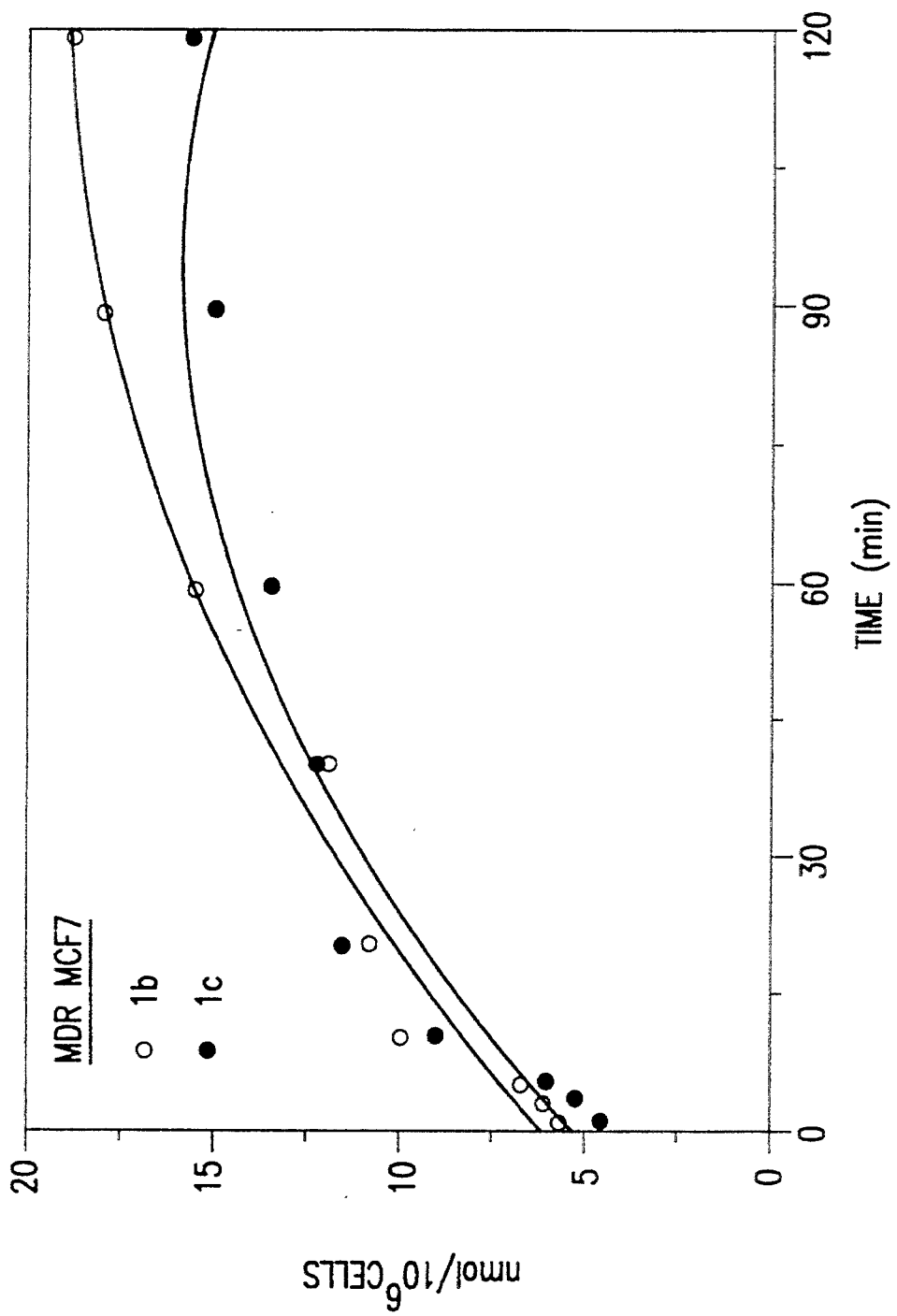
FIG. 1 is a graph of the time course of accumulation of Compounds 1b and 1c in MCF7 Adr 10 human breast cancer cells.

It has now been found that when the agents disclosed herein are used together with an antitumor agent, they enhance the therapeutic effect of the antitumor agent. It is believed that the N-substituted alkyl amino anthraquinones utilized in the present invention are better suited for clinical application than previously described resistance modifiers.

While the inventors do not wish to be bound by any theory of operation for the present invention, it is noted that the agents disclosed herein are not known to be calcium-channel blockers or calmodulin antagonists. They have not shown in vitro inhibitory activity against a number of cellular kinases. They have, however, been found to elevate the intracellular concentration of antineoplastic drugs in tumor cells overexpressing the multiple drug transporter. Sensitization of drug resistant tumors and elevation of intracellular antitumor drug concentrations probably occur by a mechanism different from calcium antagonism.

Potentiating agents disclosed herein include:

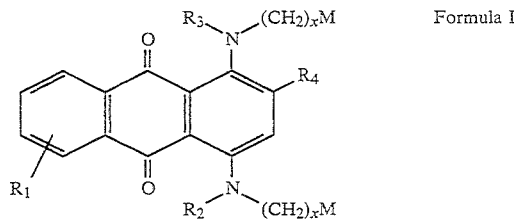

Formula I and

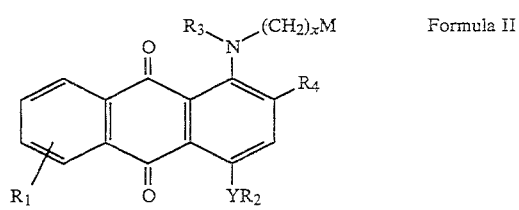

Formula II wherein:

$R_1$ is H or an alkyl chain with 1–7 carbon atoms;
$R_2$ is H or an alkyl chain with 1–7 carbon atoms;
$R_3$ is H or an alkyl chain with 1–7 carbon atoms;
$R_4$ is H or an alkyl chain with 1–7 carbon atoms;
x is an integer ranging from 3 to 12;
Y is O or NH; and
M is selected from the following groups:

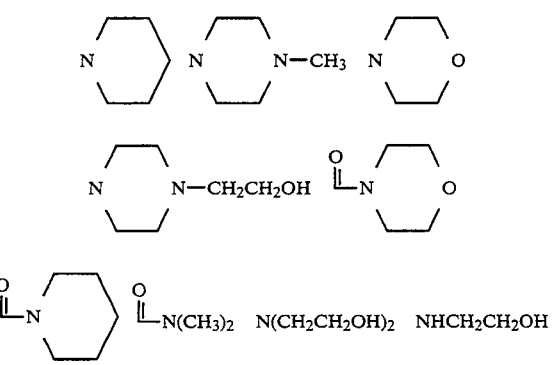

Preferably the potentiating agents are those wherein M is selected from the following groups:

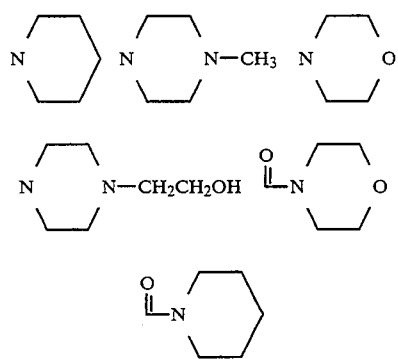

More preferably, the potentiating agents are compounds according to Formula I or a pharmaceutically acceptable salt thereof; wherein $R_1$, $R_2$, $R_3$, and $R_4$ are H.

Salts of the foregoing compounds useful in the present invention are acid addition salts, especially pharmaceutically useful nontoxic acid addition salts, such as those with inorganic acids, for example, hydrochloric, hydrobromic, nitric, sulfuric, or phosphoric acid, or with organic acids, such as organic carboxylic acids, for example, acetic, propionic, glycolic, malonic, succinic, maleic, hydroxymaleic, methylmaleic, fumaric, malic, tartaric, citric, benzoic, cinnamic, manrelic, salicylic, 4-aminosalicylic, 2-phenoxybenzoic, 2-acetoxybenzoic, embonic, nicotinic or isonicotinic, or organic sulfonic acids, for example, methanesulfonic, ethanesulfonic, 2-hydroxy-ethanesulfonic (isethionic), ethane-1,2-disulfonic, benzenesulfonic, p-toluenesulfonic, naphthalene-2-sulfonic, or cyclohexane sulfamic acid, as well as ascorbic acid.

A preferred category of drug resistant tumor cells to be treated by the method of the present invention are MDR cells, which contain P-glycoprotein, the multidrug transporter protein described in M. Gottesman and J. Pastan, supra. Thus, tumor cells treated by the present invention are preferably those characterized by (a) the expression of the multidrug transporter protein, or (b) the ability to express the multidrug transporter protein upon selection by an antineoplastic agent.

Exemplary of tumor cells which express the multidrug transporter (intrinsically resistant cells) are adenocarcinoma cells, pancreatic tumor cells, pheochromocytoma cells, carcinoid tumor cells, chronic myelogenous leukemia cells in blast crisis, renal cell, hepatocellular tumor cells, adrenal cancer cells, and colon cancer cells. Other tumor cell types may also be treated by the potentiating agents of the present invention and sensitized thereby to one or more antineoplastic agents.

Exemplary of tumor cells having the ability to express the multidrug transporter protein upon selection by an antineoplastic agent are neuroblastoma cells, adult acute lymphocytic leukemia cells, adult acute nonlymphocytic leukemia cells, nodular poorly differentiated lymphoma cells, breast cancer cells and ovarian cancer cells. A preferred group of tumor cells for treatment in the present invention are the adenocarcinomas, including adenocarcinomas of adrenal, kidney, liver, small intestine and colon tissue.

Preferred antineoplastic agents for use in the present invention are those to which multidrug transporter-mediated MDR cells develop resistance. Exemplary of such antineoplastic agents are Vinca alkaloids, epipodophyllotoxins, antibiotics, anthracycline antibiotics, actinomycin D, puromycin, gramicidin D, taxol, taxotere, colchicine, topoisomerase I and II inhibitors, cytochalasin B, emetine, maytansine, and amsacrine (or "mAMSA"). Preferred antineoplastic agents are Vinca alkaloids, epipodophyllotoxins, anthracycline antibiotics, actinomycin D, taxol, taxotere, and topoisomerase I inhibitors (camptothecin and topotecan).

The Vinca alkaloid class is described in Goodman and Gilman's The Pharmacological Basis of Therapeutics, 1277–1280 (7th ed. 1985) (hereafter "Goodman and Gilman"). Exemplary of Vinca alkaloids are vincristine, vinblastine, and vindesine.

The epipodophyllotoxin class is described in Goodman and Gilman, supra. at 1280–1281. Exemplary of epipodophyllotoxins are etoposide, etoposide orthoquinone, etoposide phosphate, and teniposide.

The anthracycline antibiotic class is described in Goodman and Gilman, supra. at 1283–1285. Exemplary of anthracycline antibiotics are daunorubicin, doxorubicin, mitoxantrone, bisantrene, epirubicin, and idarubicin. Actinomycin D, also called Dactinomycin, is described in Goodman and Gilman, supra. at 1281–1283.

The phrase "concurrently administering," as used herein, means that the antineoplastic agent and the potentiating agent are administered either (a) simultaneously (optionally by formulating the two together in a common carrier), or (b) at different times during the course of a common treatment schedule. In the latter case, the two compounds are administered at times sufficiently close for the potentiating agent to enhance the selective growth-inhibiting action of the antineoplastic agent on the tumor cells. This may be within one month, one week, one day or one hour.

Subjects to be treated by the method of the present invention include both human and animal (e.g., dog, cat, cow, horse) subjects, and are preferably mammalian subjects.

The potentiating agent is administered in an amount effective to enhance the efficacy of the antineoplastic agent. The potentiating agent is preferably administered in a total amount per day of not more than about 1 g/kg body weight, more preferably not more than about 400 mg/kg, most preferably not more than about 50 mg/kg, and most preferably not more than 5 mg/kg. With respect to minimum dose, the potentiating agent is preferably administered in a total amount per day of at least about 0.01 mg/kg, more preferably at least about 0.1 mg/kg, and most preferably at least about 1 mg/kg. The potentiating agent may be administered once or several times a day.

As noted above, the compounds of Formula (I) and (II) may be administered per se or in the form of a pharmaceutically acceptable salt. When used in medicine, the salts of the compound of Formula (I) and (II) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids, hydrochloric, hydrobromic, sulfuric, nitric, phosphoric, maleic, acetic, salicylic, p-toluenesulfonic, tartaric, citric, isethionic, methanesulphonic, formic, malonic, succinic, naphthalene-2-sulfonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the potentiating agent together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

Pharmaceutical formulations of the present invention may optionally include an antineoplastic agent, preferably an agent as described above. Such a formulation is useful for concurrently administering an antineoplastic agent and the potentiating agent in a method as described above.

The formulations include those suitable for oral, rectal, topical, nasal, ophthalmic, transdermal, or parenteral (including subcutaneous, intramuscular and intravenous) administration. Formulations suitable for oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired :formulations.

Formulations of the present invention suitable for oral administration may be presented as discrete units such as capsules, cachets, tablets or lozenges, each containing a predetermined amount of the potentiating agent as a powder or granules. Formulations for oral administration also may be a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a flee-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Opthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, as described below, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The following examples are provided to illustrate the present invention. Temperatures are given in degrees Celsius unless otherwise indicated. The following compounds were employed in the examples:

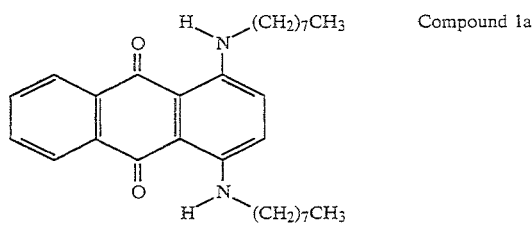

Compound 1a

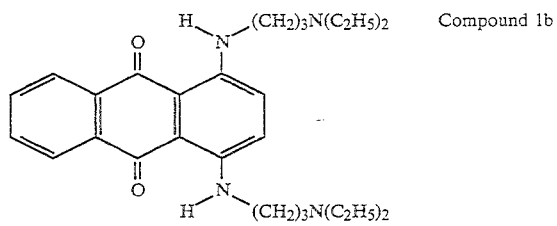

Compound 1b

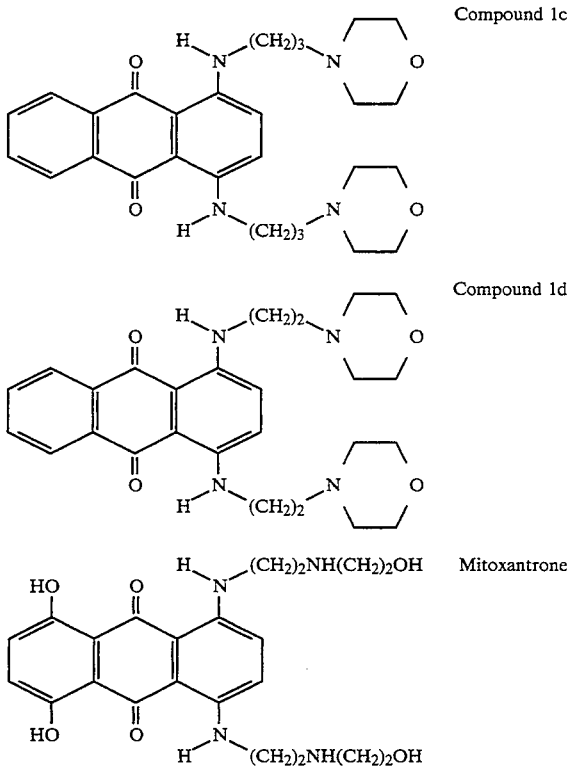

Compound 1c

Compound 1d

Mitoxantrone

EXAMPLE 1

The N-substituted diaminoanthraquinone, 1b, (1,4-bis-[[3'-(diethylamino)propyl]amino]anthraquinone), was identified as a PKC inhibitor in the micellar PKC screening assay and in platelets. This blue-colored compound had significantly greater activity in drug accumulation assays than other PKC inhibitors. Compound 1c (1,4-bis-[[3'(4-morpholino)propyl]amino]anthraquinone) had marginal PKC inhibitory activity in a preliminary screening assay. Examination of adherent cells treated with 1b or 1c revealed that treatment imparted a blue color to the monolayers. In Bligh-Dyer extracts of cells treated with 1b or 1c, the blue color was observed to quantitatively partition (>95%) with cellular phospholipids in the lower chloroform phase. Spectrophotometric analysis of 1b and 1c indicated they were excellent chromophores with absorbance maxima at 648 and 600 nm in chloroform, respectively, and extinction coefficients of approximately 20,000. At these wavelengths, there was minimal absorbance by cellular components contained in the chloroform phase. These properties of 1b and 1c were utilized to determine the time course of accumulation of these compounds in MDR MCF7 Adr 10 cells.

METHOD: Near confluent monolayers of MCF7 ADR 10 were washed 2 times with Dulbecco's Phosphate Buffered Saline (DPBS) and 1 ml of Iscove's Modified Dulbecco's Medium (IMDM) was added to each well. The monolayers were treated with 25 μM 1b or 1c and incubated at 37° C. After incubating the samples for the times indicated in FIG. 1, the monolayers were washed three times with DPBS and detached using 1 ml of Trypsin-EDTA. An aliquot of the cell suspension was counted using a Coulter Counter and a 0.8 ml aliquot was extracted in a Bligh-Dyer extraction (Bligh et at., *Can. J. Biochem.* 31:911–916 (1959)). The absorbance of the lower chloroform phase was measured at 648 nm and 600 nm using a spectrophotometer. The amount of 1b or 1c present in the extract was quantitated from a standard curve performed in cell extracts. The data is expressed as nmol anthraquinone/$10^6$ cells.

FIG. 1 shows the results of time course experiments which measured accumulation of 1b and 1c. Maximal accumulation of 1b and 1c was observed at about 2 hours.

EXAMPLE 2

The activities of 1a, 1b, 1c and 1d and mitoxantrone, an anthraquinone antineoplastic drug, were evaluated in vinblastine drug accumulation assays performed by the following method. 1,4-bis-(octylamino) anthraquinone (1a), is a compound that caused PKC stimulation in screening assays. Mitoxantrone was identified as a PKC inhibitor in miceliar PKC assays. Compound 1d (1,4-bis-[[2-(4-morpholino)ethyl]amino]anthraquinone) was only evaluated in cellular studies.

METHOD: Washed cell monolayers were incubated in 1 ml of IMDM with the indicated diaminoanthraquinones or verapamil (a positive control) for 2 hours. [$^3$H] vinblastine ([$^3$H] VLB) was added to a final concentration of 100 nM and the cells were incubated for 2.5 hours. At this time, the cells were washed 3 times in ice cold PBS and lysed in buffer containing 0.1% Triton X-100. Net accumulation of [$^3$H] vinblastine was expressed as pmol/mg protein. In [$^3$H] VLB accumulation assays, basal accumulation of cells treated with vehicle alone were negative controls ([Drug]=0) and cells treated with verapamil are positive controls.

Figure 2:
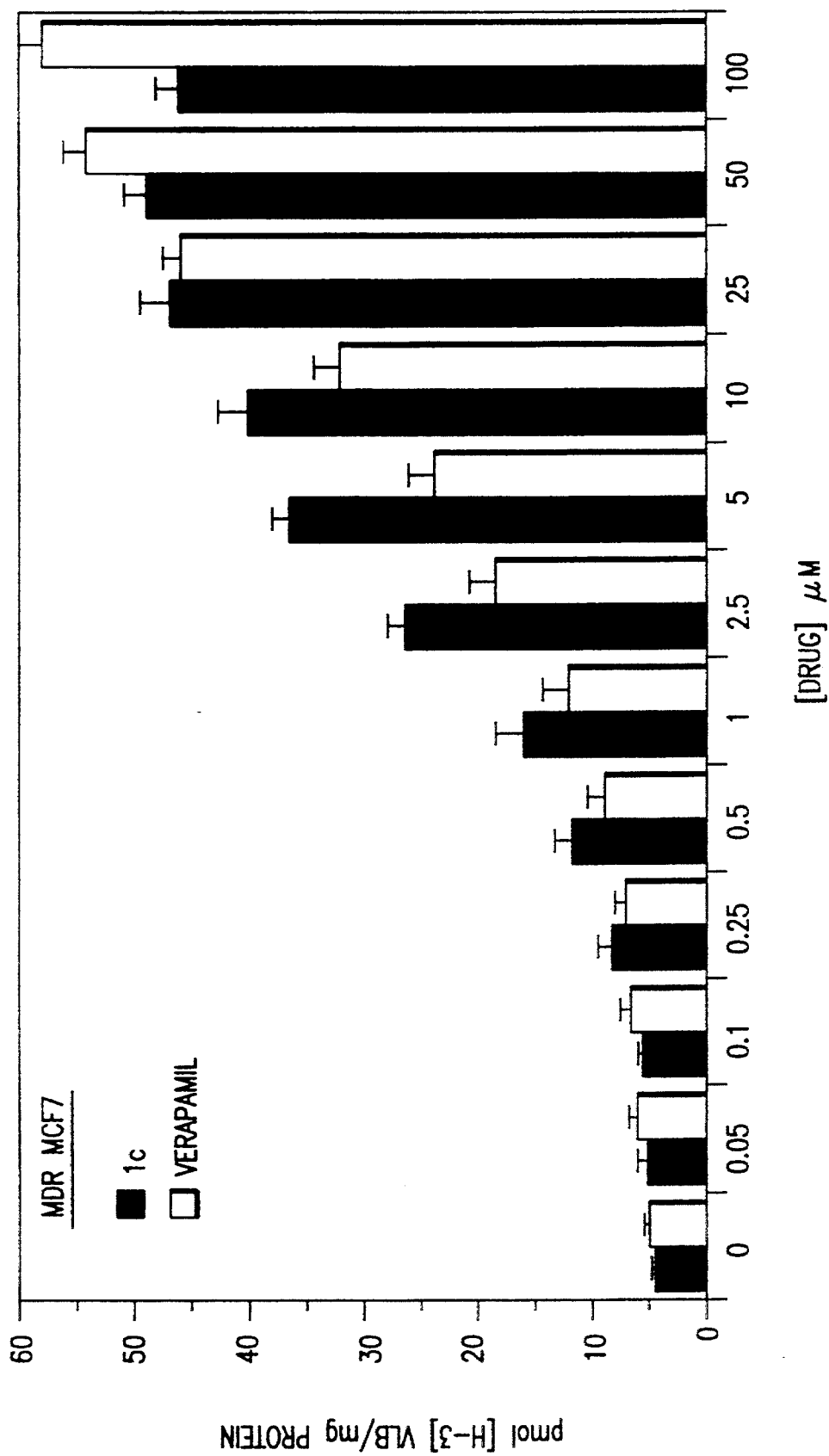
FIG. 2 is a bar graph Of the activities of vehicle controls, Compound 1c and verapamil, respectively, in MCF7 Adr 10 vinblastine accumulation assays.
Figure 3:
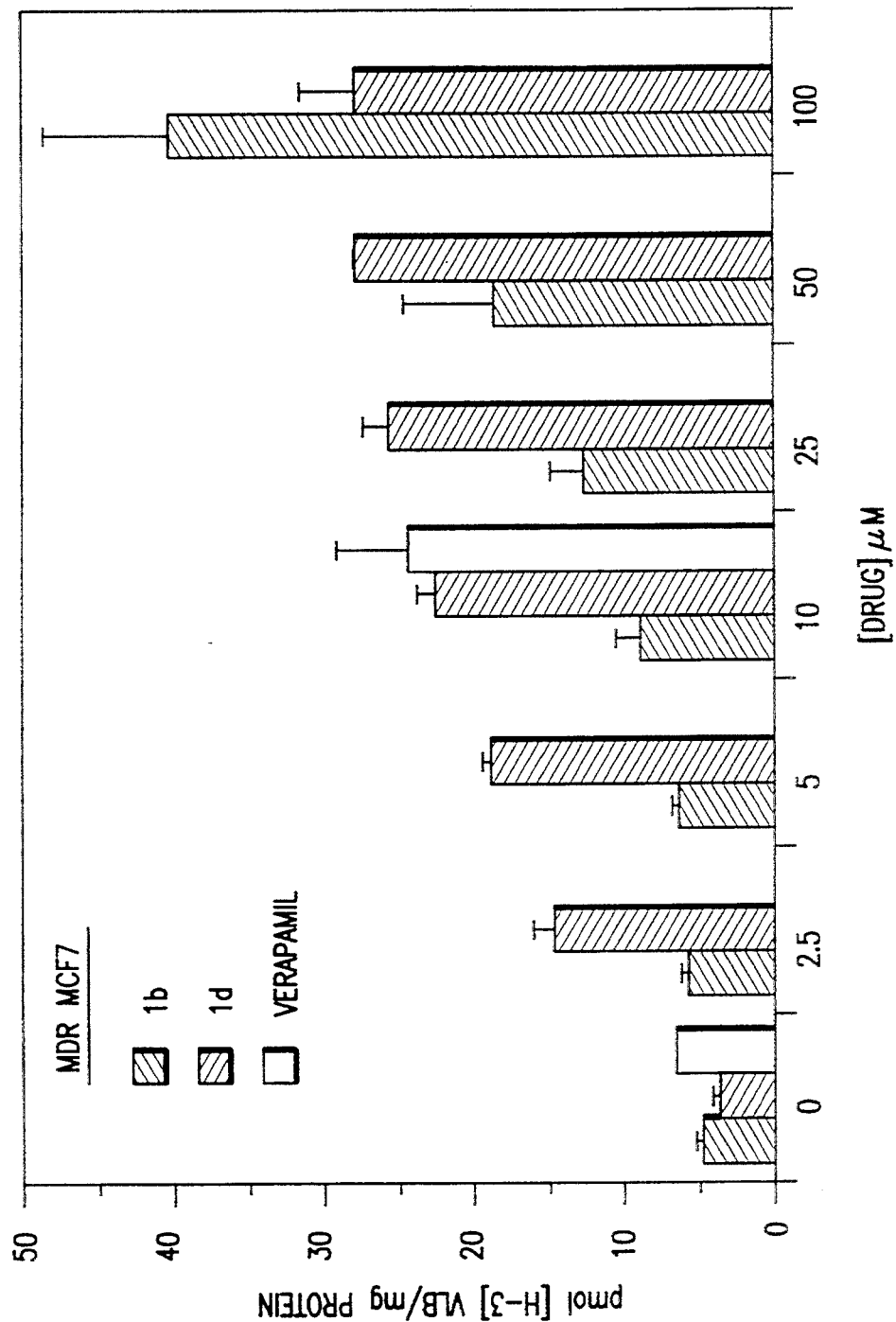
FIG. 3 is a bar graph of the activities of vehicle controls, Compounds 1b and 1d, and verapamil, respectively, in MCF7 Adr 10 vinblastine accumulation assays.

The activities of these compounds in vinblastine accumulation assays are summarized in FIGS. 2 and 3. FIG. 2 shows the results of vinblastine accumulation experiments in which the activities of 1c and verapamil are directly compared at concentrations ranging from 50 nM to 100 μM. The activities of 1b and 1,4-bis-[3'-(N-morpholino)ethylamino]anthraquinone (1d) in vinblastine accumulation assays are shown in FIG. 3. These figures show that 1b, 1c and 1d increase vinblastine accumulation in MDR MCF7, and show that 1c is the most potent compound. In addition, 1c showed activity superior to verapamil at concentrations between 0.5 μM and 10 μM. A comparison of FIGS. 2 and 3 show that the lowest concentrations of each agent which cause a doubling of basal accumulation of vinblastine are 0.5 μM for 1c, 1 μM for verapamil, 2.5 μM for 1d and 25 μM for 1b. Compound 1a and mitoxantrone did not show significant activity in this assay.

EXAMPLE 3

The activity of the most potent compound, 1c, has been evaluated in vinblastine accumulation assays with intrinsically resistant renal cell carcinoma cell lines, A704, SKRC7 and UOK-39. These cell lines are models of intrinsic resistance. They express P-glycoprotein (demonstrated by immunocytochemistry using C219 monoclonal antibody to P-glyeoprotein). In MTT proliferation assays[1], the vinblastine IC50s for these cell lines are 10–600 fold higher than the vinblastine IC50 of sensitive MCF7. In contrast to the MCF7 Adr 10 cell line, a model of acquired MDR phenotype, the resistance in these cell lines has not been selected by exposure to increasing concentrations of natural product drugs. This in vitro data is consistent with the clinical observation that renal cell carcinoma is generally unresponsive to chemotherapy. These tumors are considered intrinsically resistant (Chabner et. al., Cancer 54:2599–2608 (1984)).

[1] (3-(4,5-dimethylthiazol-2-yl)-2,5-diphenyl tetrazolium bromide). MTT, a yellow, water soluble tetrazolium dye, is reduced to an insoluble purple formazan by mitochondrial dehydrogenases in viable cells (Mosmann et at., Immunochem. Meth. 65:55–63 (1983)).

METHOD: Washed cell monolayers were incubated in 2 ml of IMDM with the indicated diaminoanthraquinones or verapamil for 2 hours. [³H] vinblastine was added to a final concentration of 10 nM and the cells were incubated for 2.5 hours. At this time, the cells were washed 3 times in ice cold PBS and lysed in buffer containing 0.1% Triton X-100.

Figure 4:
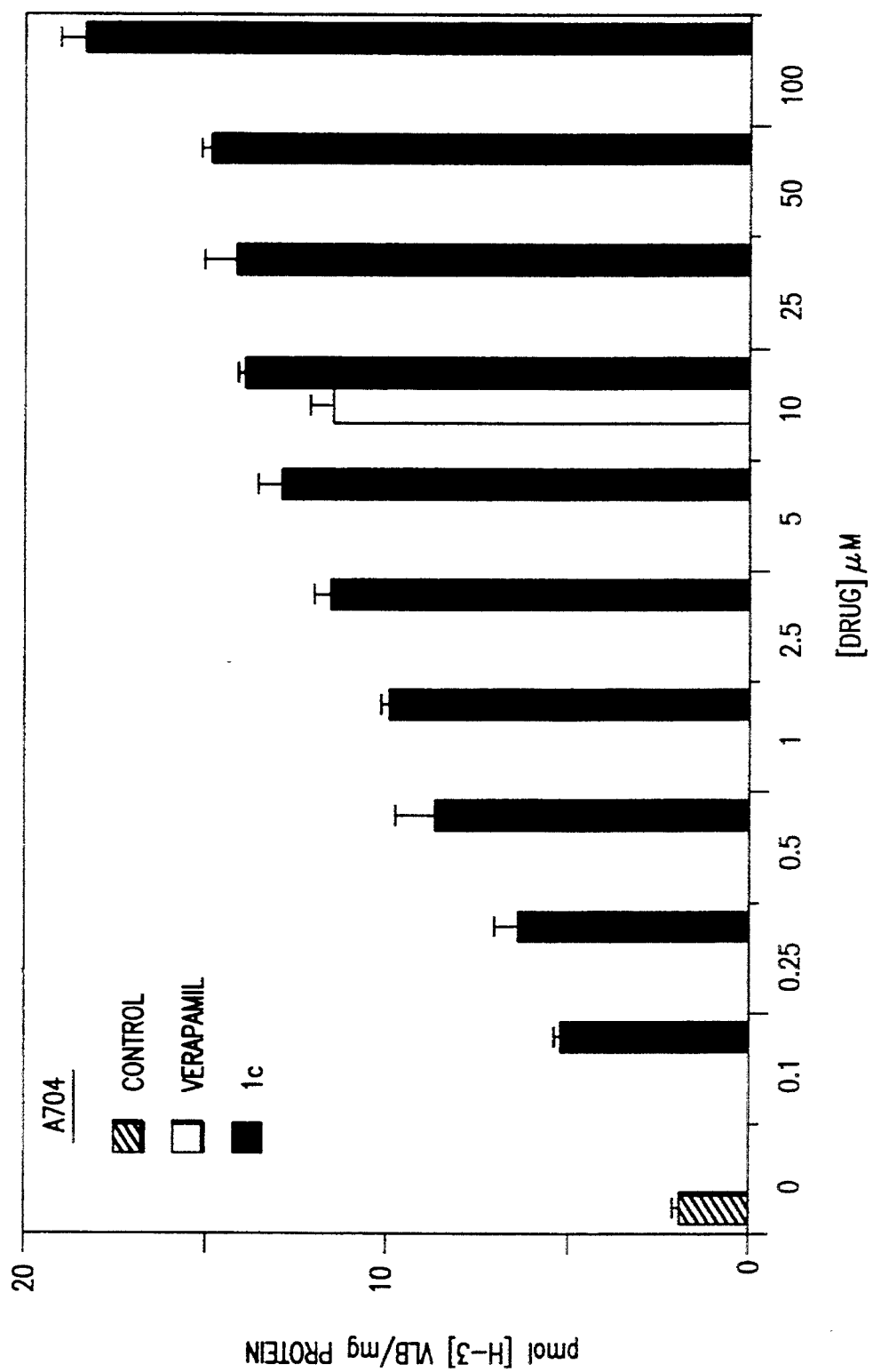
FIG. 4 is a bar graph of the activity of a vehicle control, Compounds 1c and verapamil, respectively, in A704 human renal cell line in vinblastine accumulation assays.
Figure 5:
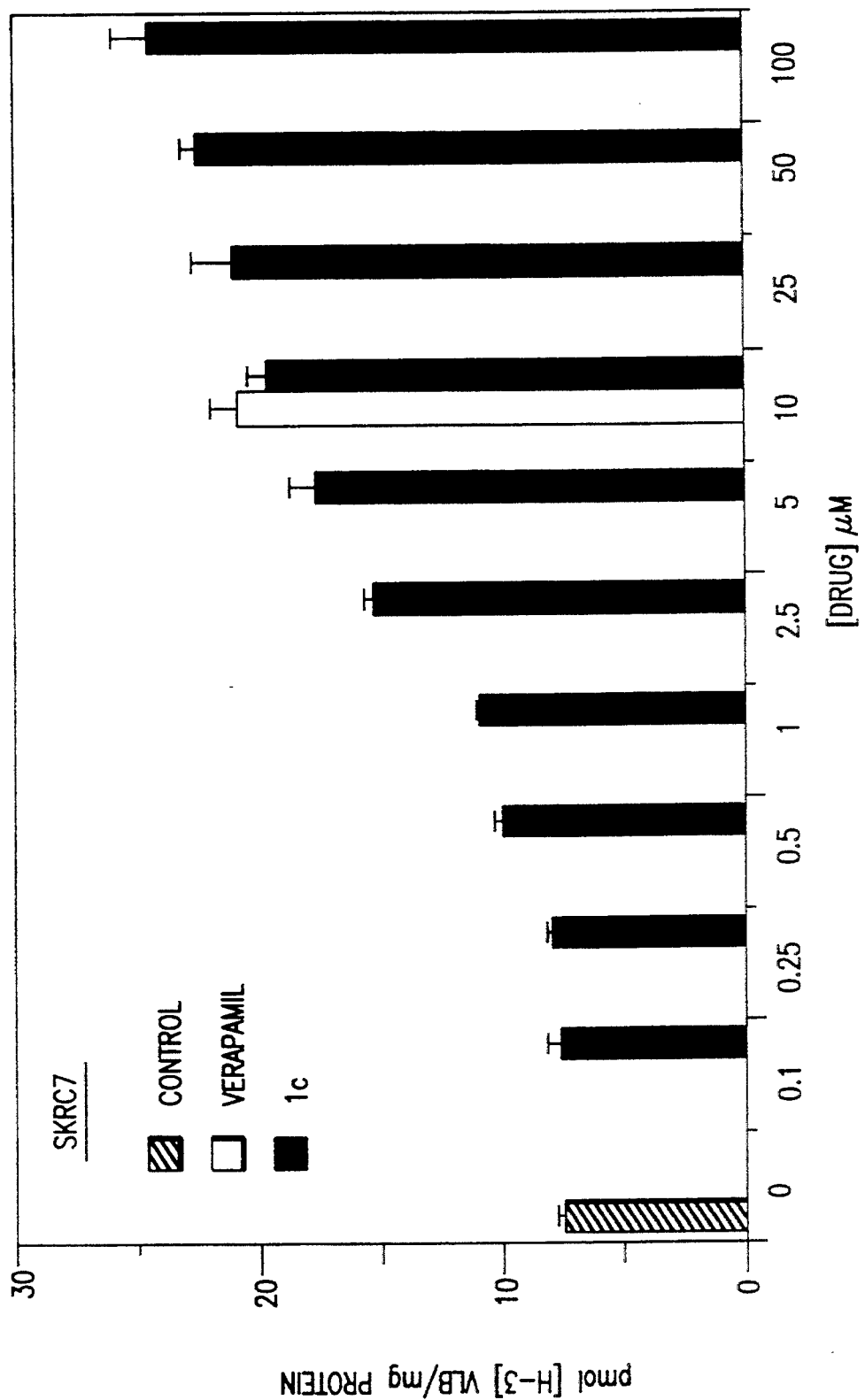
FIG. 5 is a bar graph of the activity of a vehicle control, Compound 1c and verapamil, respectively, in SKRC7 human renal cell line in vinblastine accumulation assays.
Figure 6:
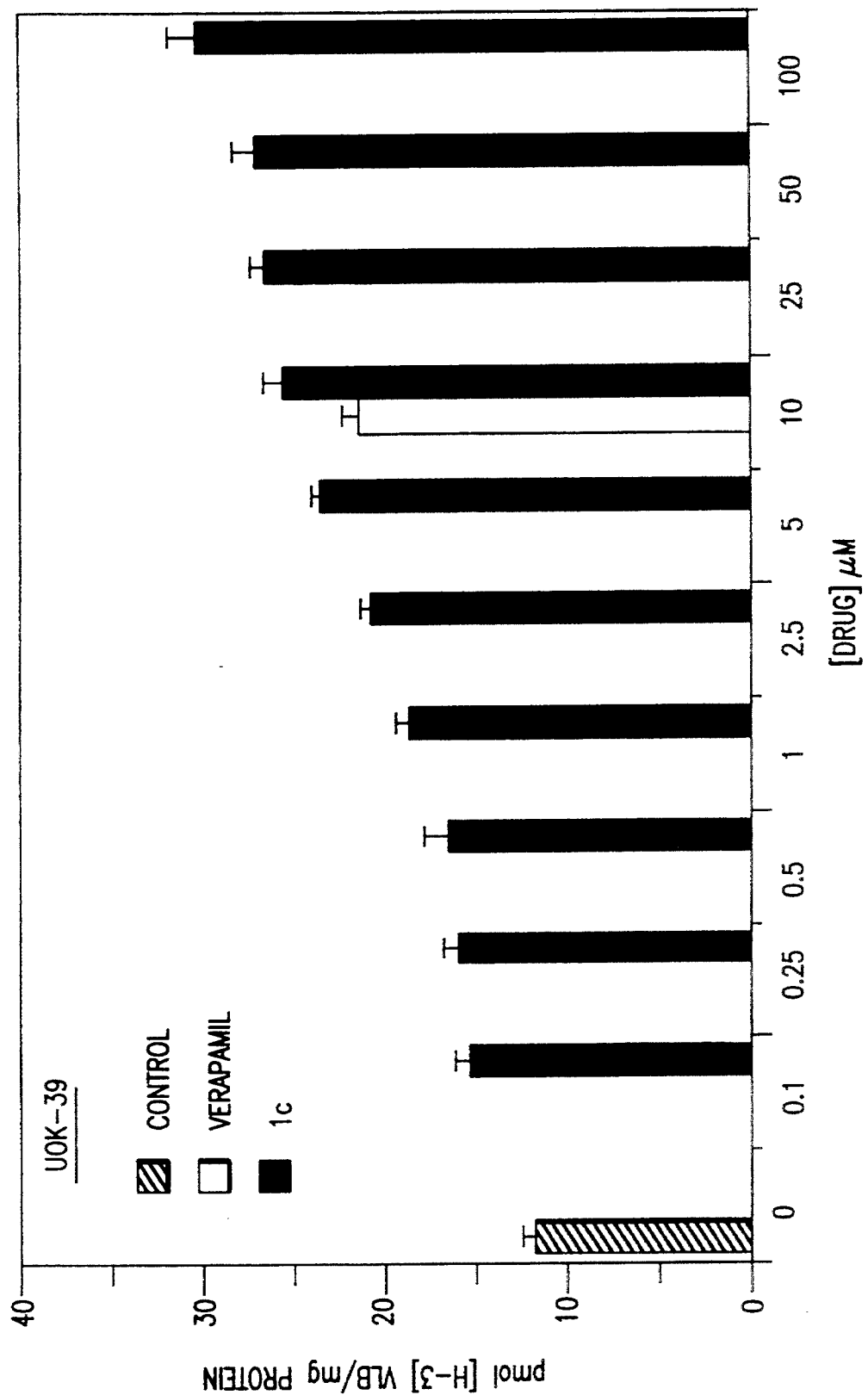
FIG. 6 is a bar graph of the activity of a vehicle control, Compound 1c and verapamil, respectively, in UOK-39 human renal cell line in vinblastine accumulation assays.
Figure 7:
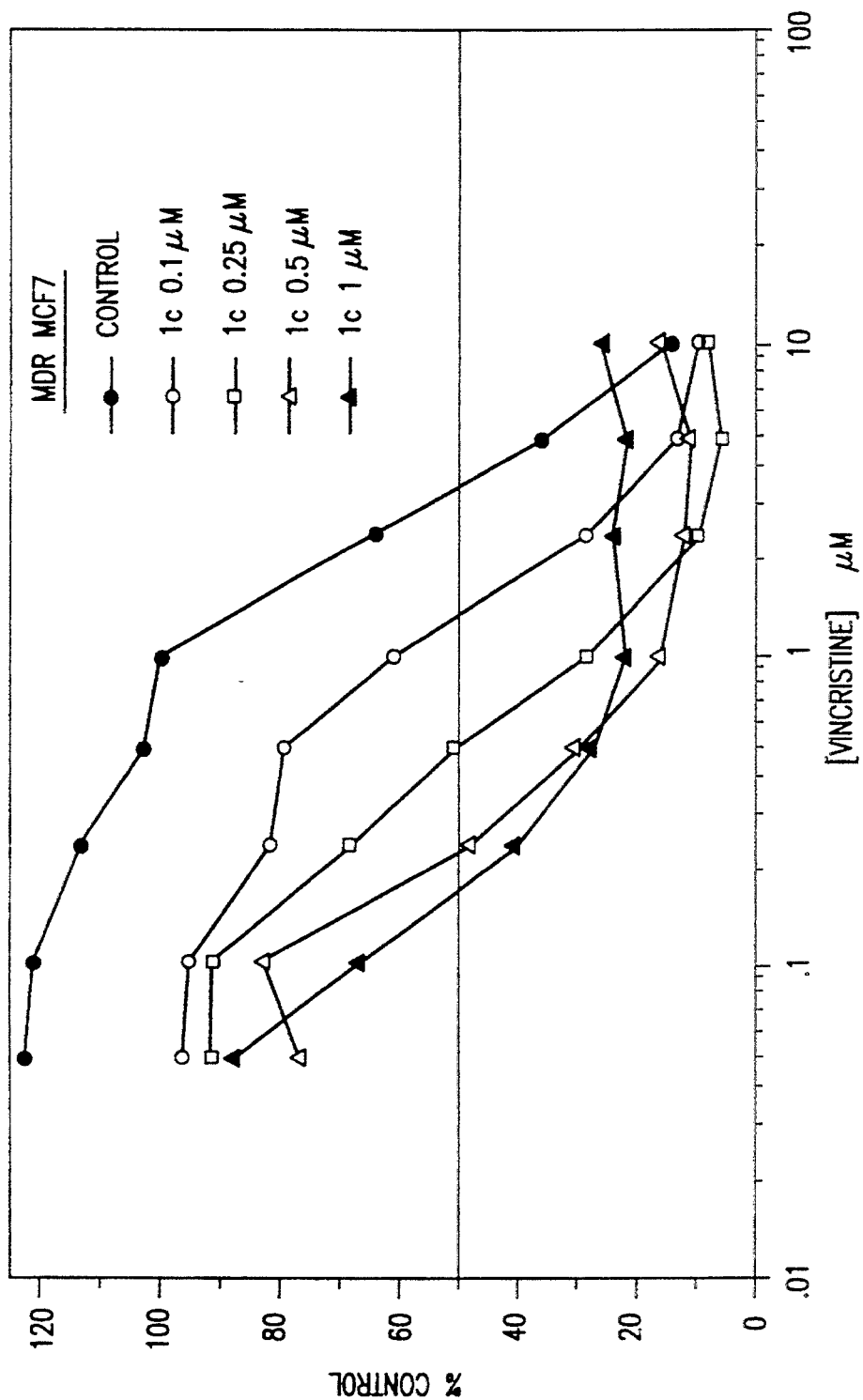
FIG. 7 is a graph of inhibition concentration (IC) curves for vincristine in MCF7 Adr 10 cell line which shows the potentiating effect on vincristine toxicity as a function of Compound 1c concentration.
Figure 8:
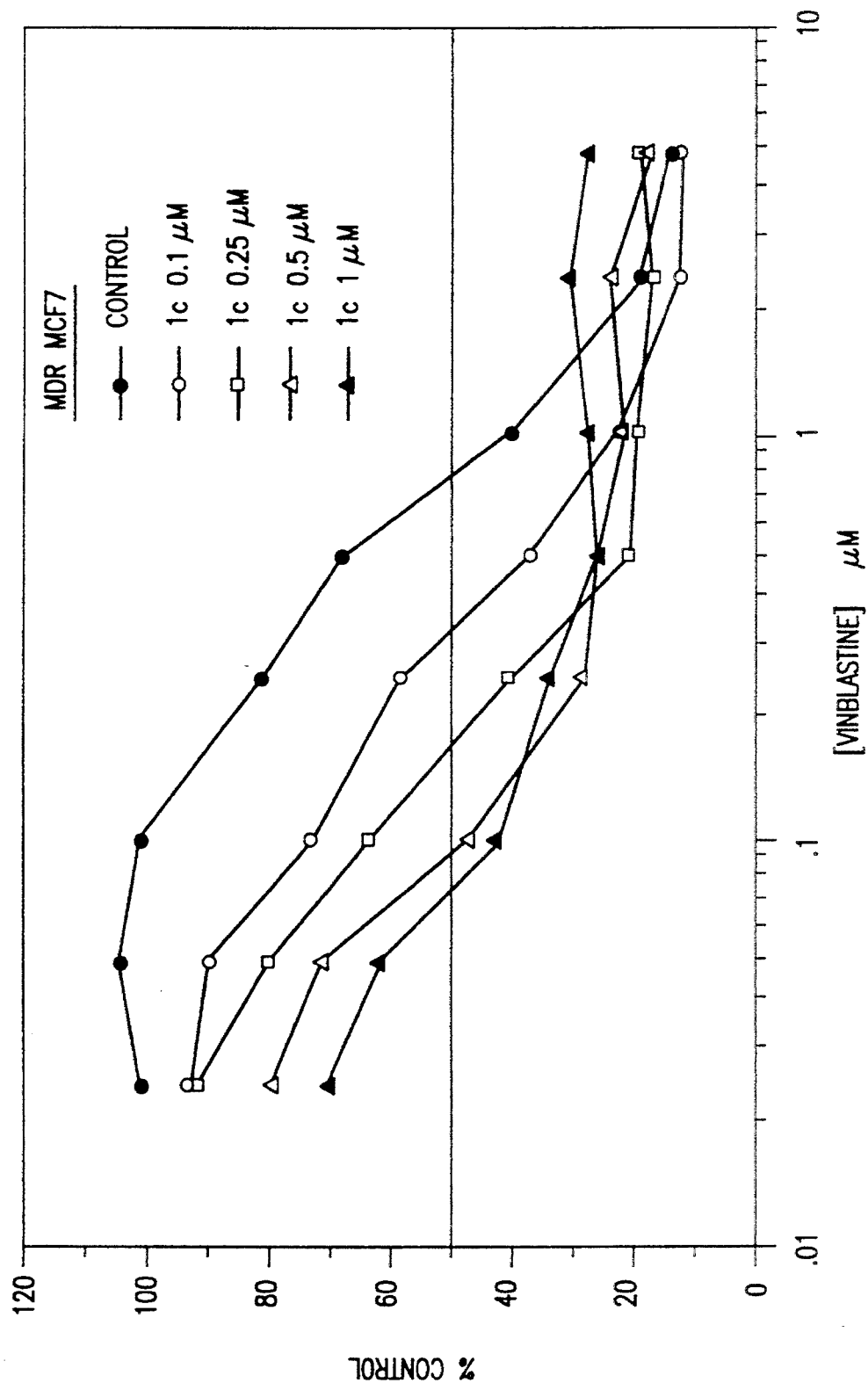
FIG. 8 is a graph of IC curves for vinblastine in MCF7 Adr 10 cell line which shows the potentiating effect on vincristine toxicity as a function of Compound 1c concentration.
Figure 9:
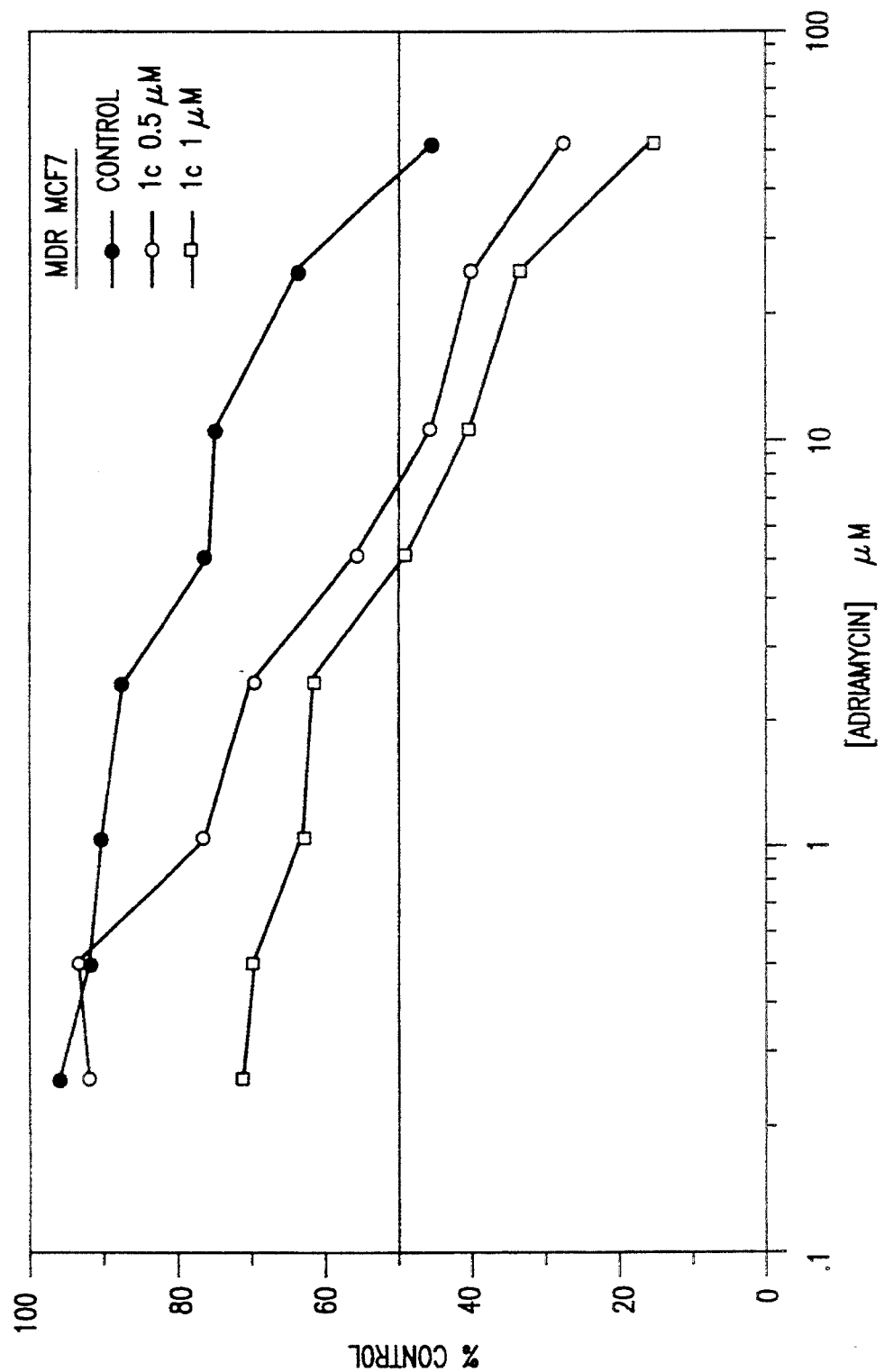
FIG. 9 is a graph of IC curves for adriamycin (doxorubicin) in MCF7 Adr 10 cell line which shows the potentiating effect on doxorubicin toxicity as a function of Compound 1c concentration.
Figure 10:
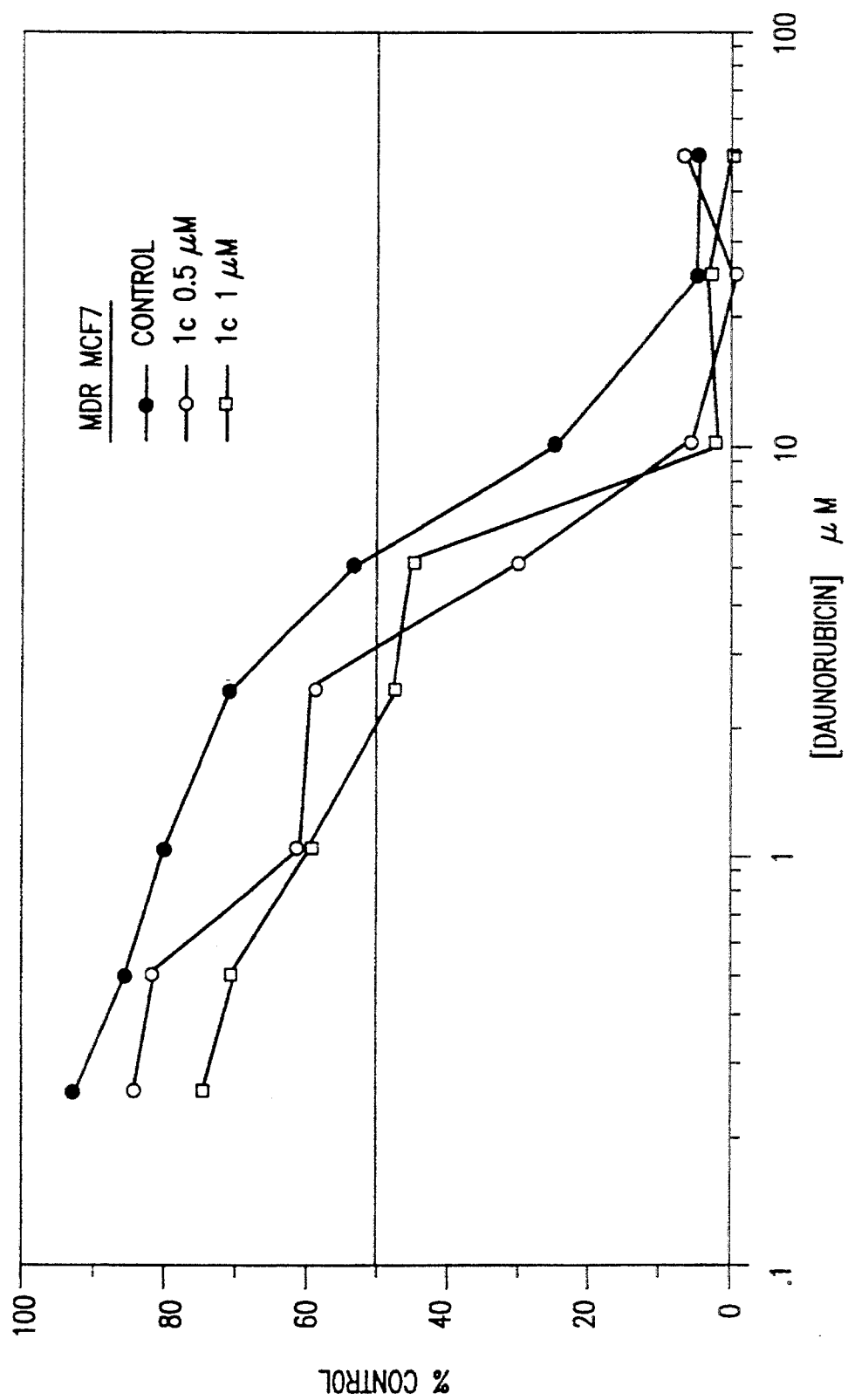
FIG. 10 is a graph of IC curves for daunorubicin in MCF7 Adr 10 cell line which shows the potentiating effect on daunorubicin toxicity as a function of Compound 1c concentration.

In FIGS. 4–6, the net accumulation of [³H] vinblastine is expressed as pmol [³H] vinblastine/mg protein. These examples show that 1c increases vinblastine accumulation in cell lines which are models of intrinsic resistance. A comparison of the activities of 1c and verapamil (a positive control) at 10 $\mu$M, shows that 1c activity is comparable or superior to verapamil activity.

EXAMPLE 4

In 72 hour MTT proliferation assays using the following method, compounds 1b, 1c and 1d were assessed for inhibition of Vinca alkaloid and anthracycline drug resistance in MDR MCF7. Additionally, compounds 1b and 1c were assessed for potentiation of sensitivity to Vinca alkaloid and anthracycline drugs in the parental MCF7 WT cell line.

METHOD: 5000 cells per well were plated in 100 $\mu$l of IMDM containing 10% FCS and allowed to adhere overnight. The following day the cells were treated with N-substituted 1,4-diaminoanthraquinones and exposed to graded concentrations of antineoplastic agents. 50 $\mu$l of IMDM 10% FCS containing either vehicle or N-substituted 1,4-diaminoanthraquinones at 3 times the final tested concentration was added to cells at timed intervals. The plates were incubated for 2 hours at 37° C. to allow maximal cellular accumulation of N-substituted 1,4-diaminoanthraquinones. 40 $\mu$l aliquots of IMDM 10% FCS containing either vehicle or graded concentrations of antineoplastic drugs at 5 times the final concentration were added to treatment groups. Following this addition, 10 $\mu$l of IMDM 10% FCS containing either vehicle or N-substituted 1,4-diaminoanthraquinone at 5 times the final concentration was added to each group of wells. The cells were incubated for 72 hours after treatment. At this time the viable cells in each treatment group were estimated in a colorimetric assay by adding MTT and incubating the cells at 37° C. for 3–4 hours. The media in each well was aspirated and MTT formazan was solubilized in isopropyl alcohol acidified with 0.1 N HCl. The absorbance of the solubilized formazan was quantitated using a plate reader spectrophotometer. Control experiments showed that the absorbance of MTT was proportional to cell number. The concentrations of antineoplastic drugs which inhibited proliferation by 50% (IC50's) were estimated by calculating a percentage from the ratio: antineoplastic drug treated groups/control group absorbance and plotting the dose response curve on semilog paper. The IC50 was estimated from this curve. To assess the effects of inhibition of resistance by N-substituted 1,4-diaminoanthraquinones, the percentages were calculated relative to cell groups treated with resistance modifier alone and IC50's calculated as above. A reversal factor was calculated by dividing the IC50 to the antineoplastic drug alone (Control group) by the IC50 to antineoplastic drug in cells treated with resistance modifier.

TABLE 1

Reversal of Vincristine (VCR) Resistance in MCF7 Adr 10 by Compound 1c

| [1c] $\mu$M | VCR IC$_{50}$ ($\mu$M) | Reversal Factor |
|---|---|---|
| 0 | 3.3 ($\pm$0.30) | 1.0 |
| 0.1 | 1.4 ($\pm$0.50) | 2.3 |
| 0.25 | 0.67 ($\pm$0.13) | 5.0 |
| 0.5 | 0.32 ($\pm$0.07) | 10.4 |
| 1.0 | 0.13 ($\pm$0.05) | 24.8 |

The data shown in Table 1 is the average ($\pm$ standard deviation) of 3 experiments.

TABLE 2

Reversal of Vinblastine (VLB) Resistance in MCF7 Adr 10 by Compound 1c

| [1c] $\mu$M | VLB IC$_{50}$ ($\mu$M) | Reversal Factor |
|---|---|---|
| 0 | 0.79 ($\pm$0.12) | 1.0 |
| 0.25 | 0.23 ($\pm$0.05) | 3.5 |
| 0.1 | 0.37 ($\pm$0.01) | 2.2 |
| 0.5 | 0.093 ($\pm$0.006) | 8.5 |
| 1.0 | 0.087 ($\pm$0.011) | 9.2 |

The data shown in Table 2 is the average ($\pm$ standard deviation) of 3 experiments.

TABLE 3

Reversal of Adriamycin (ADR) Resistance in MCF7 Adr 10 by Compound 1c

| [1c] $\mu$M | ADR IC$_{50}$ ($\mu$M) | Reversal Factor |
|---|---|---|
| 0 | 38 ($\pm$5) | 1.0 |
| 0.5 | 19 ($\pm$8) | 2.0 |
| 1.0 | 11 ($\pm$7) | 3.3 |

The data shown in Table 3 is the average ($\pm$ standard deviation) of 4 experiments.

TABLE 4

Reversal of Daunorubicin (DNR) Resistance in MCF7 Adr 10 by Compound 1c

| [1c] $\mu$M | DNR IC$_{50}$ ($\mu$M) | Reversal Factor |
|---|---|---|
| 0 | 6.7 ($\pm$1.0) | 1.0 |
| 0.5 | 3.5 ($\pm$0.3) | 1.9 |
| 1.0 | 2.1 ($\pm$0.3) | 3.2 |

The data shown in Table 4 is the average ($\pm$ standard deviation) of 3 experiments.

TABLE 5

Potentiation of Vincristine (VCR) Sensitivity in MCF7 WT by Compound 1c

| [1c] $\mu$M | VCR IC$_{50}$(nM) | Reversal Factor |
|---|---|---|
| 0 | 1.9 ($\pm$0.4) | 1.0 |
| 1.0 | 1.0 ($\pm$0.2) | 1.9 |

The data shown in Table 5 is the average ($\pm$ standard deviation) of 5 experiments.

Figure 11:
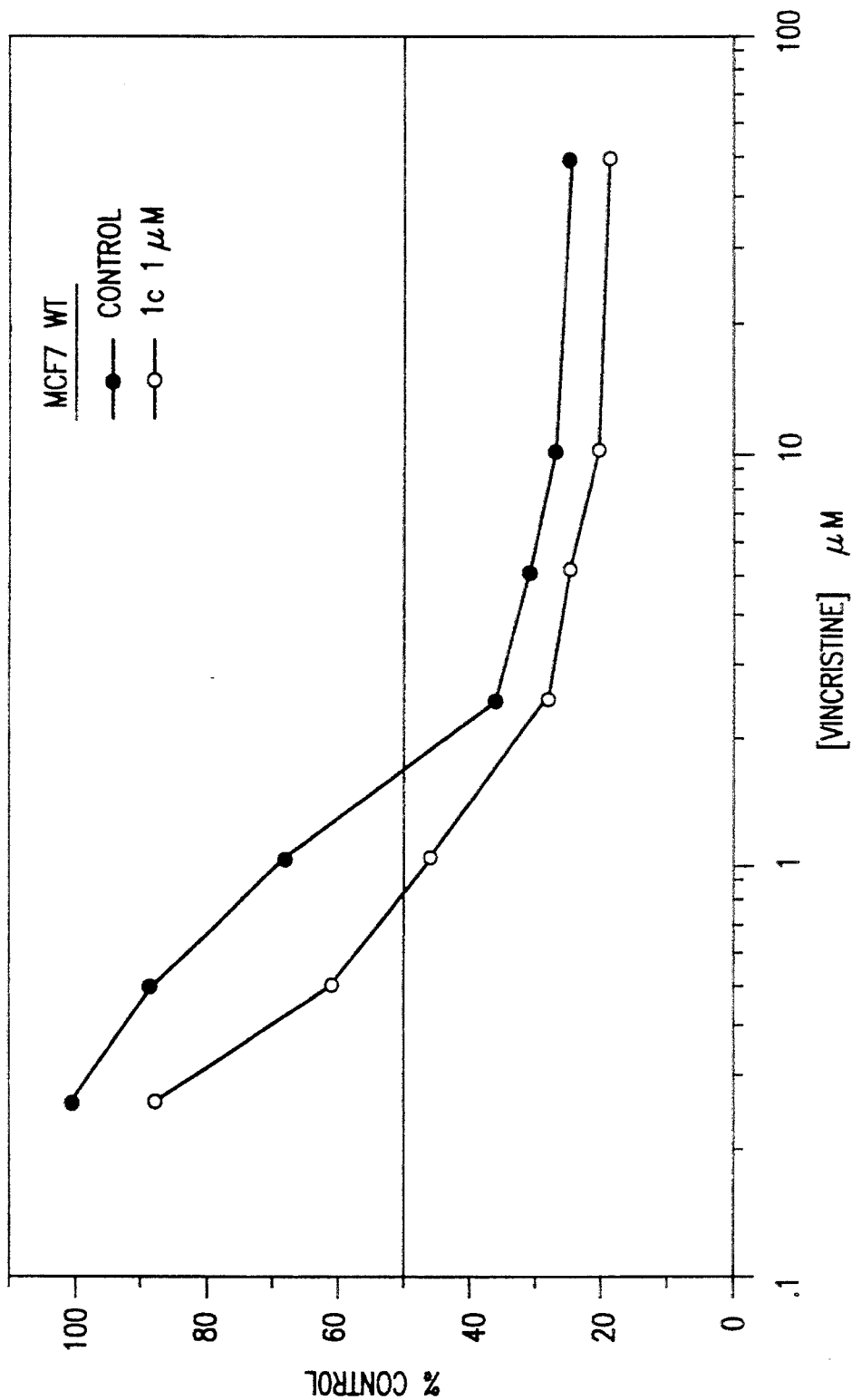
FIG. 11 is a graph of IC curves for vincristine in MCF7 WT cell line which shows the potentiating effect on vincristine toxicity as a function of Compound 1c concentration.

Comparisons of activities of 1b, 1c and 1d as inhibitors of drug resistance indicated that 1c was the most potent inhibitor of the MDR phenotype in the MCF7 Adr 10 cell line. In the inhibition concentration (IC) curves shown in FIGS. 7–10, the inhibition of drug resistance to vincristine (VCR), vinblastine (VLB), adriamycin (ADR), and daunorubicin (DNR) in MDR MCF7 by 1c in representative experiments is shown. In each case, the IC50 concentration of the respective antineoplastic drug was reduced as a function of increasing 1c concentration. Tables 1–4 relating to FIGS. 7–10, respectively, summarize the results of repeated experiments as an average ($\pm$ standard deviation) and a reversal factor. In FIG. 11 and Table 5, potentiation of vincristine sensitivity in MCF7 WT is shown. The concentrations of 1c in these experiments were not cytotoxic. In the presence of 1c alone, the average cell growth was greater than 86% (n=14) of the vehicle control at the test concentrations. In the Paired Student's t-test, the differences in the antineoplastic drug IC50s for control ([1c]=0) and 1c treated cells are significant (P<0.05).

EXAMPLE 5

The effects of compound 1c on phosphorylation of the P-glycoprotein and the MARCKS protein (myristoylated alanine-rich C kinase substrate) was studied in intact cells labeled with [$^{32}$P] orthophosphate. The MARCKS protein (also known as the 80 to 87 kD protein) is observed to be rapidly phosphorylated subsequent to PKC activation by phorbol esters, cell permeant diacylglycerols, growth factor and hormonal stimulation in a variety of cell types from several species. MARCKS displays calcium-calmodulin binding and filamentous actin crosslinking activities which are regulated by PKC mediated phosphorylation (Hartwig et al., *Nature* 356:618–622 (1992)). In these experiments, phosphorylation of MARCKS was used as a marker of cellular PKC activity. The effects of 1c on phosphorylation states of the P-glycoprotein and MARCKS protein were studied to test the possibility that this compound may be inhibiting PKC in cells; due to metabolism to an active PKC inhibitor or by achieving inhibitory concentrations in the microenvironment of the P-glycoprotein.

METHOD: A monoclonal antibody to the P-glycoprotein, C219, was used to immunoprecipitate the P-glycoprotein and a polyclonal rabbit antibody was used to immunoprecipitate the MARCKS protein from extracts of cells labeled with [$^{32}$P]. MARCKS was immunoprecipitated after preclearing the aliquot with normal rabbit IgG. MCF7 Adr 10 cells were labeled with [$^{32}$P] orthophosphate for two hours. At timed intervals, cells were treated with 1c and incubated for 10 minutes to two hours. All samples were labeled for a total of 4 hours at which time the samples were washed and lysed in an extraction buffer containing detergents, protease inhibitors and phosphatase inhibitors. The samples were matched by TCA precipitable counts. P-glycoprotein and MARCKS were immunoprecipitated from aliquots of the same sample containing equivalent radioactivity.

Figure 12:
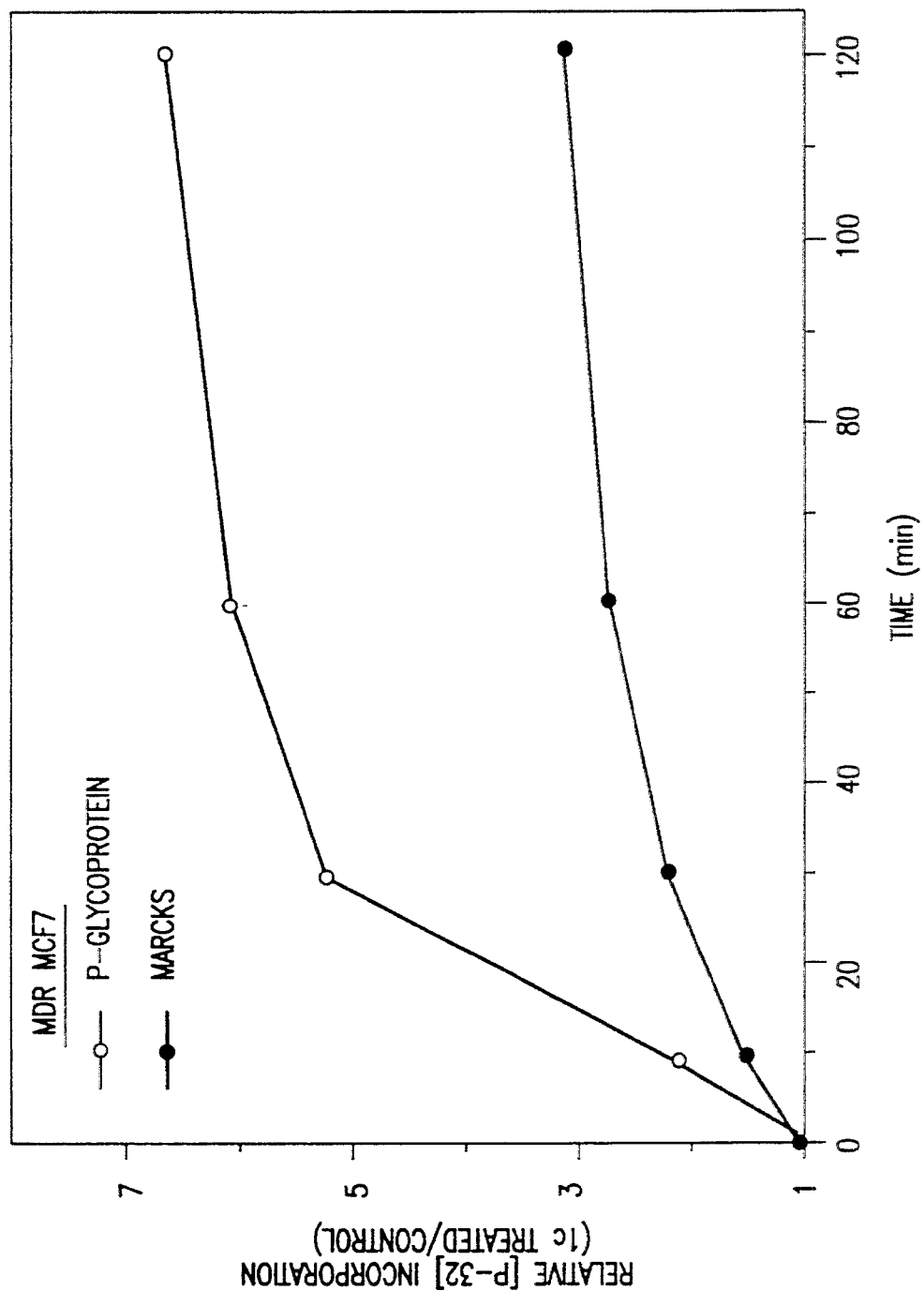
FIG. 12 is a graph of the time course of Compound 1c stimulated phosphorylation of P-glycoprotein and MARCKS, respectively, in MDR MCF7 cells
Figure 13:
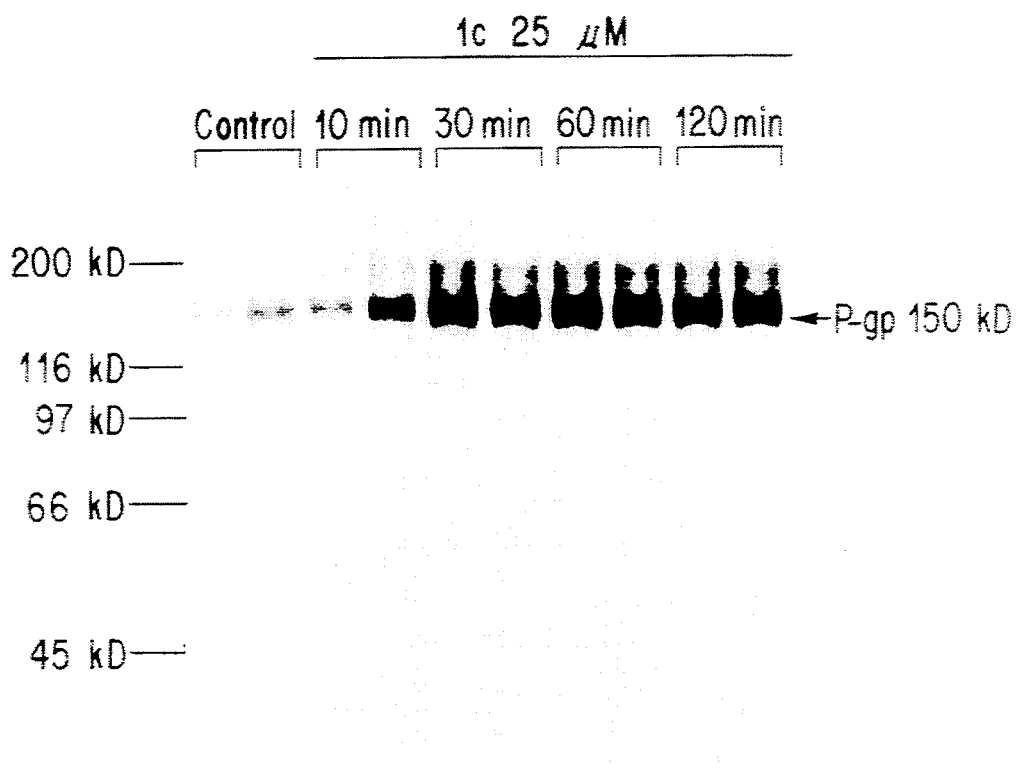
FIG. 13 is an audioradiograph of the time course of Compound 1c stimulated phosphorylation of P-glycoprotein in MCF7 Adr 10 cell line.
Figure 14:
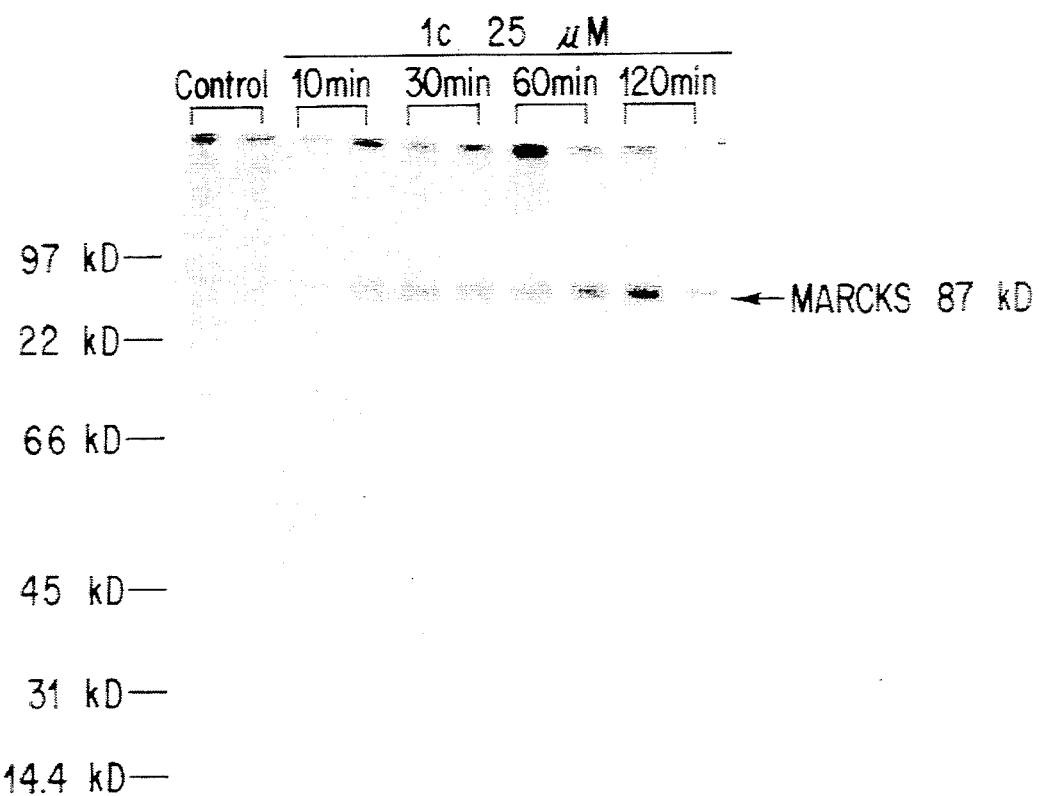
FIG. 14 is an autoradiograph of the time course of Compound 1c stimulated phosphorylation of MARCKS in MCF7 Adr 10 cell line.

The summary of densitometric studies of a representative time course experiment with 1c is shown in FIG. 12. Autoradiographs of this experiment shown in FIGS. 13 and 14 show that 1c increases both P-glycoprotein and MARCKS phosphorylation, 6.6-fold and 3-fold, respectively (FIG. 12). There is a good correlation between the time course of 1c accumulation measured spectrophotometrically from the organic phase of Bligh-Dyer extracts (FIG. 1) and the time course of P-glycoprotein and MARCKS phosphorylation (FIG. 12). These results suggest that 1c is not inhibiting PKC in intact cells. Previously, phorbol myristate acetate, an activator of PKC, and verapamil and trifluoperazine, resistance modifiers which bind to the P-glycoprotein and non-specifically inhibit PKC in vitro, have been found to stimulate phosphorylation of the P-glycoprotein at serine residues on different sites of the P-glycoprotein (Hamada et al., *Cancer Res.* 47:2860–2865 (1987)).

Compound 1c was evaluated for inhibitory activity against a variety of cellular kinases including casein kinase 2, the catalytic subunits of protein kinase A and calmodulin kinase; but 1c did not inhibit these kinases. One possible explanation for stimulation of phosphorylation of P-glycoprotein and MARCKS is that 1c may activate PKC or other cellular kinases by signal transduction pathways that have not yet been identified to phosphorylate these proteins. An alternative explanation for stimulation of phosphorylation of P-glycoprotein and MARCKS is that 1c inhibits protein phosphatases. Analysis of overall phosphoprotein changes in cell extracts indicates that treatment with 1c did not significantly alter phosphorylation of other phosphoproteins.

EXAMPLE 6

The effects of 1c on specific binding of [$^3$H] VLB to membrane vesicles from sensitive and MDR MCF7 have been studied using the method described below. These studies indicate that 1c inhibits vinblastine binding to the P-glycoprotein.

METHOD: Membrane vesicles from sensitive and MDR MCF7 were prepared by nitrogen cavitation and isolated by centrifugation in discontinuous sucrose gradients. SDS-PAGE analysis of membrane vesicles from sensitive and resistant MCF7 cells shows a 160 kD protein which is present in membrane vesicles from resistant cells and absent in MCF7 wt cells. This band can be immunoprecipitated by C219 antibody to P-glycoprotein indicating that membrane vesicles from MDR cells contain the P-glycoprotein and membrane vesicles from MCF7 WT do not. In the presence of 100 nM [$^3$H] VLB and ATP, total and nonspecific binding of [$^3$H] VLB (experimentally defined as binding in the presence of a 100 μM unlabeled VLB) was measured. Association of [$^3$H] VLB with membrane vesicles of MCF7 Adr 10 in a rapid filtration assay was: (1) maximal by 15 min. at room temperature; (2) inhibited by addition of unlabeled VLB; and (3) enhanced, approximately 2–3 fold, by addition of ATP. In contrast, association of [$^3$H] VLB to membrane vesicles of MCF7 WT was approximately 15 % of MCF7 Adr 10 and addition of ATP did not significantly enhance association of [$^3$H] VLB with MCF7 WT vesicles.

Previous studies have shown that membrane vesicles from MDR cells show specific and saturable binding of Vinca antineoplastic drugs (Hamada et al., *J. Biol. Chem.* 263:1454–1458, 1988; Cornwell et at., *J. Biol. Chem.* 261: 7921–7928 (1986); and Cornwell et al., *Proc. Natl. Acad. Sci., USA* 83:3847–3850 (1986)). Thus, the differences in association of [$^3$H] VLB with membrane vesicles of MCF7 WT and MCF7 Adr 10 are probably related to binding of [$^3$H] VLB by the P-glycoprotein in membrane vesicles of the MDR cells.

Specific binding of [$^3$H] VLB to MCF7 Adr 10 membrane vesicles was 27.4 pmol/mg protein. It was determined by subtracting non-specific binding from total binding. In the presence of 1c at 5, 10, and 25 μM, specific binding was decreased by 29, 42 and 69%, respectively. 1c had no effect on non-specific binding of [$^3$H] VLB to MCF7 Adr 10 vesicles, or the small specific binding of [$^3$H] VLB to MCF7 WT membrane vesicles. These observations suggest that modulation of the MDR phenotype by 1c may be a result of inhibition of binding of natural product drugs by P-glycoprotein. Thus, both binding and phosphorylation of P-glycoprotein may be important in modulation of the MDR phenotype by 1c.

EXAMPLE 7

Myelosuppression is often a dose limiting side effect of chemotherapeutic agents. Generally, most anticancer drugs are more or equally toxic to bone marrow granulocyte-macrophage progenitors (CFU-GM) than to cancer cells (Fine et at., *J. Clin. Oncol.* 5:489-493 (1986)). The toxicities to human granulocyte-macrophage progenitors (CFU-GM) of 1b, 1c, and VLB was assessed by measuring inhibition of CFU-GM proliferation in cultures continuously exposed to each agent alone and compared to the toxicities to sensitive and resistant MCF7 in tumor cell clonogenic assays.

METHOD: The CFLI-GM assay measures clonal proliferation of granulocyte/macrophage precursors in semisolid agar cultures. The progeny of the granulocyte/macrophage precursors remain in proximity of the progenitor cells and form colonies. Colonies which contain greater than 40 cells after 10-12 days of culture are counted using an inverted phase contrast microscope. The tumor cell clonogenic assays measure clonal proliferation of tumor cells. In this assay, 300-500 cells are plated in 10 cm² wells, allowed to adhere overnight, and are treated the following day. Tumor cell colonies were counted after 10-12 days of culture. The times of exposure in these experiments are similar; however, the concentrations of FCS are 20% in the CFU-GM assay and 10% in the tumor cell clonogenic assays. The IC50's are calculated as described above for the MTT proliferation assays. (See Example 4).

In Table 6, the IC50s for 1c, 1b and VLB in MCF7 WT and MCF7 ADR 10 cells clonogenic assays are compared to the IC50s in the CFU-GM bone marrow assay. To facilitate this comparison, a CFLI-GM toxicity index was calculated by dividing the CFU-GM IC50 by the respective tumor cell clonogenic IC50's in sensitive and resistant cells. A comparison of the IC50s in clonogenic assays of sensitive MCF7 WT and MDR MCF7 Adr 10 to the natural product drugs adriamycin (ADR), vinblastine (VLB) and vincristine (VCR) in Table 6 indicate that much higher concentrations of these drugs were required for cytotoxicity in the MCF7 Adr 10 line which exhibit the MDR phenotype. A comparison of the IC50s to vinblastine for CFU-GM, sensitive and MDR MCF7 indicates that vinblastine is approximately twice as toxic to CFU-GM as it is to the drug sensitive WT cancer cells and 1000 times more toxic to CFU-GM than to the MDR cells. The CFU-GM toxicity indices shown for vinblastine are less than 1, indicating that vinblastine is more toxic to CFU-GM than to sensitive and MDR MCF7. MCF7 WT are more sensitive to cytotoxicity of 1b than MDR MCF7 and both tumor lines were 2 to 3.5 fold more sensitive to 1b cytotoxicity than CFU-GM as indicated by CFU-GM toxicity indices which are greater than 1. In contrast, MDR MCF7 are twice as sensitive to 1c cytotoxicity as MCF7 WT and CFU-GM are approximately 10 to 20 times less sensitive to 1c cytotoxicity than drug sensitive (WT) and MDR cancer cell lines. These observations suggest that 1c has a large therapeutic index for bone marrow toxicity versus tumor cell toxicity, especially for MDR cells.

TABLE 6

A Comparison of Human Cancer Cell And CFU-GM Toxicity

| DRUG | MCF7 WT | MCF7 ADR 10 | CFU-GM |
|---|---|---|---|
| | Continuous Exposure IC50 | | |
| 1b | 0.4 μM | 0.7 μM | 1.4 μM |
| 1c | 0.8 μM | 0.4 μM | 7.8 μM |
| VLB | 0.59 nM | 0.21 nM | 0.28 nM |
| ADR | 5.6 nM | 3.4 μM | — |
| VCR | 0.4 nM | 0.97 μM | — |

TABLE 6-continued

A Comparison of Human Cancer Cell And CFU-GM Toxicity

| DRUG | MCF7 WT | MCF7 ADR 10 | CFU-GM |
|---|---|---|---|
| | CFU-GM IC50 Tumor Cell Clonogenic IC50 (CFU-GM Toxicity Index) | | |
| 1b | 3.5 | 2.0 | |
| 1c | 9.8 | 19.5 | |
| VLB | 0.47 | 0.001 | |

EXAMPLE 8

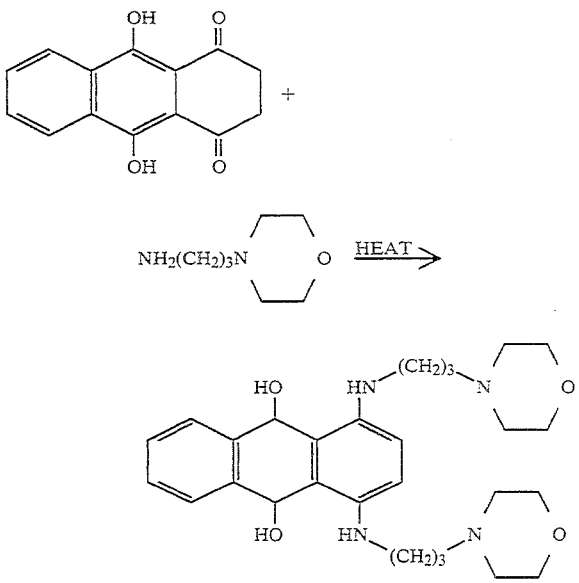

A mixture of leucoquinazarin (2,3-dihydro-9,10-dihydroxy-1,4-anthracenedione, 24.2 g, 0.1 tool) and 4-(3-aminopropyl)morpholine, 57.6 g, 0.4 mol) was heated at 50° C. under an atmosphere of $N_2$ for 90 min. The mixture was cooled and allowed to stand overnight. The oily residue was taken up in 600 ml of $CH_3OH$, and air was bubbled through the mixture at 50° C. for 3 h. After removal of the solvent under reduced pressure, the residue was purified by column chromatography on silica gel (1.5 kg). Elution with 5 % $CH_2Cl_2$ in hexane gave 13.5 g pure product. A second fraction collected (20.3 g) contained trace impurity. The first fraction was recrystallized from EtOH to give 11.3 g of pure sample: mp 134°-136° C., $^1$H NMR (CDCl$_3$, 250 MHz) δ 1.93 (m, 4), 2.49 (m, 12), 3.50 (m, 4), 3.74 (m, 8), 7.29 (s, 2), 7.69 (m, 2), 8.34 (2, m).

Anal. calc'd for $C_{28}H_{36}N_4O_4$ (492.61): C, 68.27; H, 7.37; N, 11.38. Found: C, 68.35; H, 7.53; N, 11.28.

In summary, aminoanthraquinone resistance modifiers have been identified which have the structural and functional features of a generally described MDR phenotype pharmacophore. Specifically, they are lipophilic compounds with planar aromatic domains and a basic nitrogen atom. The present data indicate that inhibition of the drug accumulation defect of MDR cells by aminoanthraquinones is influenced by the following structural characteristics. First, a nitrogen is required in the alkyl side chain[2] for activity. Compound 1a which lacks a nitrogen in the alkyl side chain is inactive. Second, the presence of a hydrophilic group, such as a heterocyclic ring, on the alkyl side chain is associated with greater activity than hydrophobic groups, such as branched alkyl chains. Compound 1c, with a heterocyclic morpholino functional group has greater activity than 1b with branched ethyl chains. Third, the position of the alkyl side chain nitrogen relative to the amino anthraquinone ring is important. Compound 1c with three carbon atoms between the nitrogen atoms[3] is a more potent MDR phenotype inhibitor than 1d which has two carbon atoms between the nitrogen atoms.[4] Finally, hydroxy substitutions at the 9, 10 positions of anthraquinone ring and on the ethyl side chains of mitoxantrone are associated with a significant loss of activity.

[2] i.e., M in Formalae I and II.
[3] i.e., x=3
[4] i.e., x=2

The activity of these compounds in vinblastine accumulation assays does not correlate with in vitro inhibition of serine threonine kinases. Mitoxantrone shows greater inhibitory activity in in vitro assays of PKC and casein kinase 2 than 1b or 1c, but does not increase drug accumulation. However, unlike 1c, 1a, 1b and 1d, mitoxantrone does not partition into the lower chloroform phase. It partitions into the upper methanol:water phase indicating that it is much less lipophilic. In contrast, 1c, the most potent inhibitor of the MDR phenotype, shows the greatest activity in drug accumulation assays but does not show significant activity in in vitro assays of serine threonine kinases.

In contrast to verapamil, phenothiazines, thioxanthenes or reserpine analogs which inhibit the MDR phenotype at between 2–10 μM (Ford et at., Cancer Res. 50:1748-1756 (1990); Zamora et al., Mol. Pharmacol. 33:454–462 (1988); Pearce et al., Proc. Natl. Acad. Sci., USA, 86:5128-5132 (1989); and Ford et at., Pharmacol. Rev. 42:155-198 (1990)), compound 1c inhibits the MDR phenotype at concentrations between 100 nM and 1 μM and enhances toxicity of vincristine in drug sensitive cells. The antiproliferative effects of compound 1c alone in clonal proliferation assays are approximately 10 and 20 times greater, respectively, in sensitive and MDR cancer cells than in human CFU-GM. These studies suggest that 1c has a large therapeutic index for bone marrow toxicity versus cancer cell toxicity.

We claim:

1. A method of reducing drug-resistance in a subject having a drug-resistant cancer, said method comprising: administering to the subject a drug-resistance reducing amount of a potentiating agent, wherein said potentiating agent is a compound selected from the group consisting of a compound of Formula (I), a compound of Formula (II), a pharmaceutically acceptable salt thereof and combinations thereof, wherein

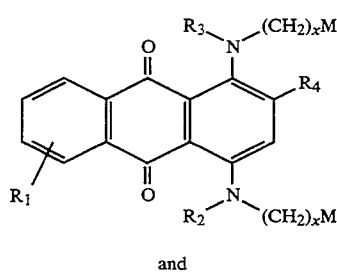

Formula I and

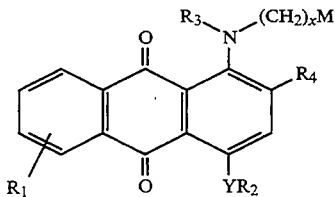

Formula II wherein:
$R_1$ is H or an alkyl chain with 1-7 carbon atoms;
$R_2$ is H or an alkyl chain with 1-7 carbon atoms;
$R_3$ is H or an alkyl chain with 1-7 carbon atoms;
$R_4$ is H or an alkyl chain with 1-7 carbon atoms;
x is an integer ranging from 3 to 12;
Y is O or NH; and
M is selected from the group of moieties consisting of:

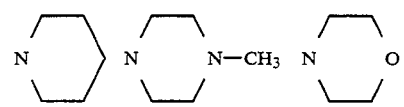

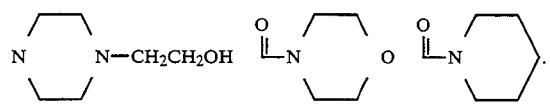

2. The method of claim 1, wherein the potentiating agents are compounds according to Formula I, or a pharmaceutically acceptable salt thereof, or combinations thereof, and wherein $R_1$, $R_2$, $R_3$, and $R_4$ are H.

3. A pharmaceutical composition for the potentiation of the effect of anticancer drugs, said composition comprising a potentiating agent together with a pharmaceutically acceptable carrier or diluent, and an antineoplastic drug, wherein said potentiating agent is a compound selected from the group consisting of a compound of Formula (I), or a pharmaceutically acceptable salt thereof or combinations thereof, wherein

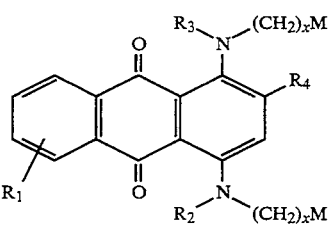

Formula I wherein:
$R_1$, $R_2$, $R_3$, and $R_4$ are H;
x is an integer ranging from 3 to 12;
Y is O or NH; and
M is selected from the group consisting of:

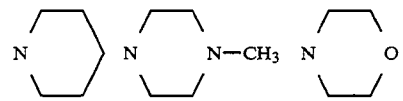

-continued

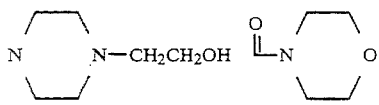

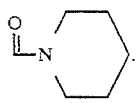

4. A method for sensitizing multidrug resistant tumor cells to an antineoplastic drug, said method comprising: administering to multidrug resistant tumor cells an effective sensitizing amount of a potentiating agent and an effective anti-tumor amount of an antineoplastic drug, wherein said potentiating agent is a compound selected from the group consisting of a compound of Formula (I), a compound of Formula (II), a pharmaceutically acceptable salt thereof and combinations thereof, wherein

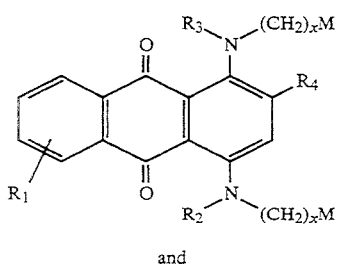

and

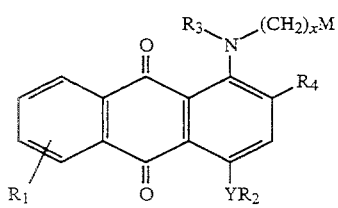

wherein:
$R_1$ is H or an alkyl chain with 1–7 carbon atoms;
$R_2$ is H or an alkyl chain with 1–7 carbon atoms;
$R_3$ is H or an alkyl chain with 1–7 carbon atoms;
$R_4$ is H or an alkyl chain with 1–7 carbon atoms;
x is an integer ranging from 3 to 12;
Y is O or NH; and
M is selected from the group consisting of:

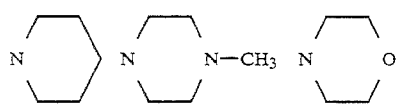

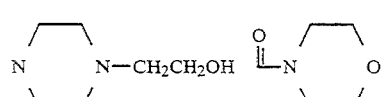

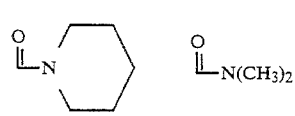

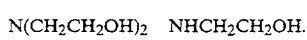

5. The method of claim 4, wherein the antineoplastic drug is selected from the group consisting of Vinca alkaloids, anthracyclines, antibiotics, epipodophlotoxins, topoisomerase I and II inhibitors, taxol, taxotere, and taxol derivatives.

6. The method of claim 4, wherein M is selected from the group consisting of:

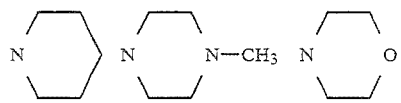

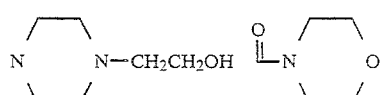

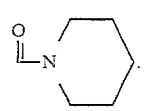

7. The method of claim 6, wherein the potentiating agents are compounds according to Formula I or a pharmaceutically acceptable salt thereof or combinations thereof, wherein $R_1$, $R_2$, $R_3$, and $R_4$ are H.

8. A pharmaceutical formulation comprising an effective antitumor amount of an antineoplastic agent and an effective sensitizing amount of a potentiating agent, wherein said potentiating agent sensitizes multidrug resistant tumor cells to said antitumor agent and wherein said potentiating agent is a compound selected from the group consisting of a compound of Formula (I), a compound of Formula (II), a pharmaceutically acceptable salt thereof and combinations thereof, wherein

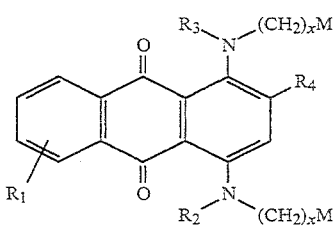

and

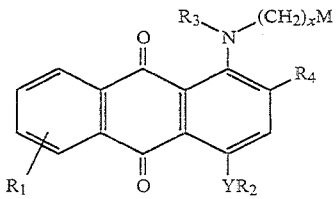

wherein:
$R_1$ is H or an alkyl chain with 1–7 carbon atoms;
$R_2$ is H or an alkyl chain with 1–7 carbon atoms;
$R_3$ is H or an alkyl chain with 1–7 carbon atoms;
$R_4$ is H or an alkyl chain with 1–7 carbon atoms;
x is an integer ranging from 3 to 12;
Y is O or NH; and
M is selected from the group consisting of:

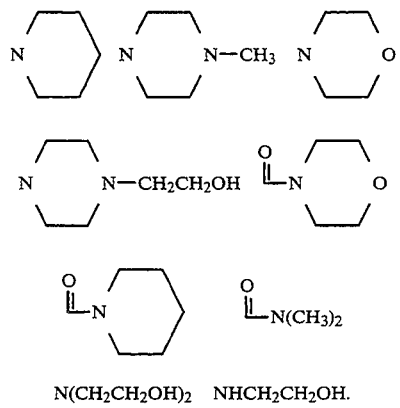

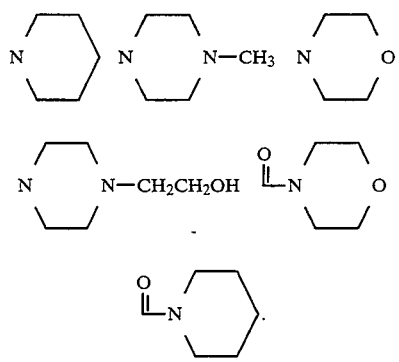

N(CH₂CH₂OH)₂    NHCH₂CH₂OH.

9. The formulation of claim 8, wherein the antineoplastic drug is selected from the group consisting of Vinca alkaloids, anthracyclines, antibiotics, epipodophlotoxins, topoisomerase I and II inhibitors, taxol, taxotere, and taxol derivatives.

10. The formulation of claim 8, wherein M is selected from the group consisting of:

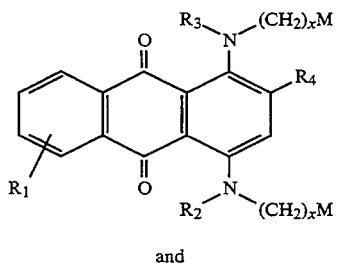

11. The formulation of claim 8, wherein the potentiating agents are compounds according to Formula I or a pharmaceutically acceptable salt thereof or combinations thereof, and wherein $R_1$, $R_2$, $R_3$, and $R_4$ are H.

12. A method of selectively inhibiting the growth of tumor cells in a subject in need of such treatment, said method comprising:
administering to said subject an effective amount of an anticancer drug independently or in combination with a potentiating agent, wherein said potentiating agent is a compound selected from the group consisting of a compound of Formula (I), a compound of Formula (II), a pharmaceutically acceptable salt thereof and combinations thereof, wherein

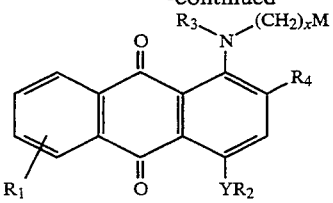

and

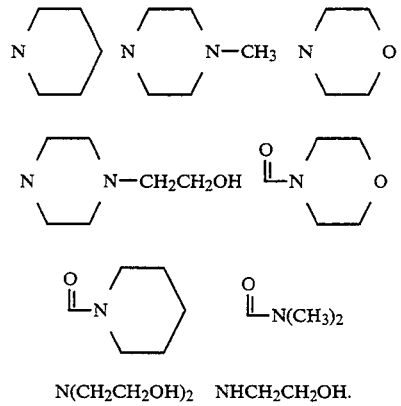

Formula II wherein:
$R_1$ is H or an alkyl chain with 1–7 carbon atoms;
$R_2$ is H or an alkyl chain with 1–7 carbon atoms;
$R_3$ is H or an alkyl chain with 1–7 carbon atoms;
$R_4$ is H or an alkyl chain with 1–7 carbon atoms;
x is an integer ranging from 3 to 12;
Y is O or NH; and
M is selected from the group consisting of:

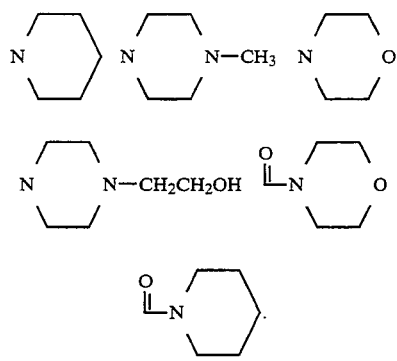

N(CH₂CH₂OH)₂    NHCH₂CH₂OH.

13. The method of claim 12, wherein the antineoplastic drug is selected from the group consisting of Vinca alkaloids, anthracyclines, antibiotics, epipodophlotoxins, topoisomerase I and II inhibitors, taxol, taxotere, and taxol derivatives.

14. The method of claim 12, wherein the amount of the potentiating agent administered ranges from about 1 to about 400 mg/kg/day in a single or divided dose.

15. The method of claim 12, wherein M is selected from the group consisting of:

16. The method of claim 12, wherein the potentiating agents are compounds according to Formula I or a pharmaceutically acceptable salt thereof or combinations thereof, and wherein $R_1$, $R_2$, $R_3$, and $R_4$ are H.

17. A method for sensitizing tumor cells to an antineoplastic drug, said method comprising:

administering to said tumor cells an effective sensitizing amount of a potentiating agent and an effective anti-tumor amount of said antineoplastic drug, wherein said potentiating agent is a compound selected from the group consisting of a compound of Formula (I), a compound of Formula (II), a pharmaceutically acceptable salt thereof and combinations thereof, wherein

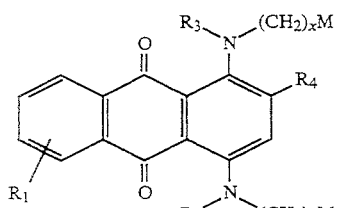

Formula I and

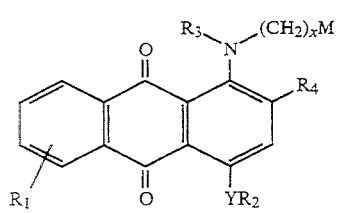

Formula II wherein:

$R_1$ is H or an alkyl chain with 1–7 carbon atoms;
$R_2$ is H or an alkyl chain with 1–7 carbon atoms;
$R_3$ is H or an alkyl chain with 1–7 carbon atoms;
$R_4$ is H or an alkyl chain with 1–7 carbon atoms;
x is an integer ranging from 3 to 12;
Y is O or NH; and
M is selected from the group consisting of:

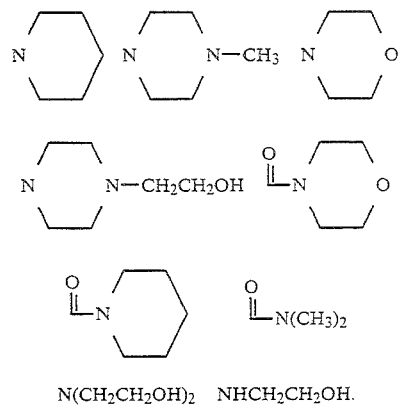

$N(CH_2CH_2OH)_2$   $NHCH_2CH_2OH$.

18. The method of claim 17, wherein the antineoplastic drug is a Vinca alkaloid.

19. The method of claim 17, wherein M is selected from the group consisting of:

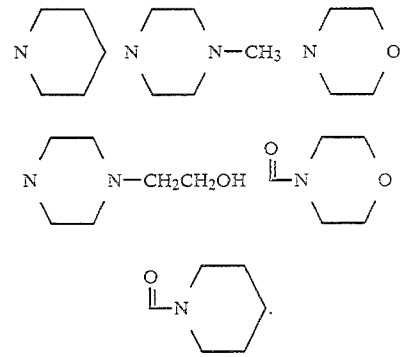

20. The method of claim 19, wherein the potentiating agents are compounds according to Formula I or a pharmaceutically acceptable salt thereof or combinations thereof; and wherein $R_1$, $R_2$, $R_3$, and $R_4$ are H.

* * * * *

UNITED STATES PATENT AND TRADEMARK OFFICE
CERTIFICATE OF CORRECTION

PATENT NO. : 5,436,243
DATED : July 25, 1995
INVENTOR(S) : Clifford W. Sachs, Robert L. Fine, Lawrence M. Ballas, F. Ivy Carroll, and Robert Bell It is certified that error appears in the above-indentified patent and that said Letters Patent is hereby corrected as shown below:

ON THE TITLE PAGE

Item [75], delete the initial "R" in the name of the fourth inventor and replace with the initial "F".

Item [73], the assignee should read as follows:
--Duke University and Sphinx Pharmaceuticals Corporation, both of Durham, N.C.; Research Triangle Institute, Research Triangle Park, N.C.--.

Signed and Sealed this

Twenty-fourth Day of October, 1995

Attest:

BRUCE LEHMAN

*Attesting Officer*  *Commissioner of Patents and Trademarks*